United States Patent
Kato et al.

(10) Patent No.: US 6,174,459 B1
(45) Date of Patent: Jan. 16, 2001

(54) DIFLUOROPHENYL DERIVATIVE COMPOUND, LIQUID CRYSTAL COMPOSITION AND LIQUID CRYSTAL DISPLAY DEVICE

(75) Inventors: Takashi Kato; Shuichi Matsui; Kazutoshi Miyazawa; Yasusuke Hisatsune; Etsuo Nakagawa, all of Chiba (JP)

(73) Assignee: Chisso Corporation, Osaka (JP)

( * ) Notice: Under 35 U.S.C. 154(b), the term of this patent shall be extended for 0 days.

(21) Appl. No.: 09/230,949

(22) PCT Filed: Aug. 19, 1997

(86) PCT No.: PCT/JP97/02871

§ 371 Date: Feb. 4, 1999

§ 102(e) Date: Feb. 4, 1999

(87) PCT Pub. No.: WO98/07674

PCT Pub. Date: Feb. 26, 1998

(30) Foreign Application Priority Data

Aug. 21, 1996 (JP) ........................................... 8-238361

(51) Int. Cl.[7] ........................... C09K 19/12; C09K 19/30; C09K 19/34; C07C 19/08; C07C 41/00
(52) U.S. Cl. .................. 252/299.66; 252/299.63; 252/299.61; 570/127; 568/631
(58) Field of Search ............... 252/299.66, 299.63, 252/299.61; 570/12; 568/631; 546/339; 544/298; 549/369

(56) References Cited

U.S. PATENT DOCUMENTS

| | | | |
|---|---|---|---|
| 5,641,429 | * 6/1997 | Reiffenrath et al. | 252/299.61 |
| 5,718,840 | * 2/1998 | Plach et al. | 252/299.66 |
| 5,723,068 | * 3/1998 | Hachiya et al. | 252/299.63 |
| 5,762,828 | * 6/1998 | Tanaka et al. | 252/299.63 |
| 5,811,029 | * 9/1998 | Wachtler et al. | 252/299.63 |
| 5,858,275 | * 1/1999 | Matsui et al. | 252/299.63 |
| 5,932,138 | * 8/1999 | Plach et al. | 252/299.66 |
| 5,948,318 | * 9/1999 | Miyazawa et al. | 252/299.63 |
| 5,948,319 | * 9/1999 | Tanaka et al. | 252/299.66 |
| 5,985,171 | * 11/1999 | Rieger et al. | 252/299.63 |
| 5,993,692 | * 11/1999 | Tarumi et al. | 252/299.63 |

FOREIGN PATENT DOCUMENTS

| | | |
|---|---|---|
| 0 291 949 | 11/1988 | (EP) . |
| 0 391 591 | 10/1990 | (EP) . |
| 0 439 089 | 7/1991 | (EP) . |
| 0 497 176 | 8/1992 | (EP) . |
| WO 91 03445 | 3/1991 | (WO) . |
| WO 91 08184 | 6/1991 | (WO) . |
| WO 96 05159 | 2/1996 | (WO) . |
| WO 97 06124 | 2/1997 | (WO) . |

* cited by examiner

Primary Examiner—C. H. Kelly
(74) Attorney, Agent, or Firm—McDermott, Will & Emery

(57) ABSTRACT

A difluorophenyl derivative compound having characteristics of a liquid crystal represented by the following general formula (1), a liquid crystal composition and a liquid crystal display device in which the composition is used:

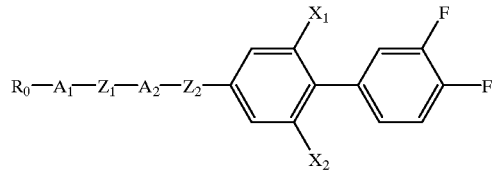

(1)

wherein $R_0$ is an alkyl group or an alkenyl group having 1 to 15 carbon atoms, and an optional methylene group in the alkyl group or the alkenyl group may be substituted by an oxygen atom; $A_1$ and $A_2$ are each a trans-1,4-cyclohexylene group, or one group selected from the group consisting of a 1,4-phenylene group, a pyrimidine-2,5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl in which one or more hydrogen atoms on a six-membered ring may be substituted by halogen atoms; $Z_1$ and $Z_2$ are each —$(CH_2)_4$—, —$(CH_2)_3O$—, —$O(CH_2)_3$— or a single bond; and $X_1$ and $X_2$ are each H, F, Cl or Br.

10 Claims, No Drawings

DIFLUOROPHENYL DERIVATIVE COMPOUND, LIQUID CRYSTAL COMPOSITION AND LIQUID CRYSTAL DISPLAY DEVICE

TECHNICAL FIELD

The present invention relates to a difluorophenyl derivative compound which is useful as a liquid crystal display material. More specifically, the present invention relates to a novel compound which has a butylene group and/or a propyleneoxy group and a 3,4-difluorophenyl group and which can express some physical properties suitable as a liquid crystal display material, a liquid crystal composition containing the compound, and a liquid crystal display device constituted by the use of the liquid crystal composition.

BACKGROUND ART

Heretofore, there have been manufactured many display devices utilizing a refractive index anisotropy, a dielectric anisotropy and the like which are characteristics of a liquid crystal. The liquid crystal display devices have widely been utilized in watches, electronic calculators, word processors, televisions and the like, and the demand of the liquid crystal display devices is increasing year by year. A liquid crystal phase lies between a solid phase and a liquid phase. This liquid crystal phase can be roughly classified into a nematic phase, a smectic phase and a cholesteric phase. The display devices utilizing the nematic phase among these liquid crystal phases have been most extensively utilized of late.

As display systems in which an electro-optical effect of the liquid crystal is applied to the liquid crystal display, there are a twisted nematic type (TN type), a dynamic scattering type (DS type), a guest-host type (GH type), a DAP type and the like. In particular, the coloring of the liquid crystal display has remarkably progressed in recent years. In the case of the TN type, display systems for the color display are mainly a thin film transistor type (TFT type) and a super-twisted nematic type (STN type), and the display devices having these display systems have been mass-produced.

Many liquid crystal compounds inclusive of compounds which are now under research steps are known, but there does not exist any liquid crystal compound which can be used in the display devices singly instead of a mixture of the liquid crystal compounds. A property which is required for the liquid crystal compound for use in the display device is that the compound shows the liquid crystal phase in the widest possible natural temperature range including typical room temperature at which the display device is most often used.

Furthermore, it is also be required that the liquid crystal compound is sufficiently stable to environmental factors and have physical properties enough to drive the display device. However, any liquid crystal compound which can meet all of these requirements singly has not been found so far.

At present, several kinds of liquid crystal compounds or non-liquid crystal compounds are mixed to prepare a composition having the above characteristics, and the thus prepared composition is put to practical use as the liquid crystal material for the display. The liquid crystal composition is required to be stable to water, light, heat, air and the like present under a usual use environment, as described above. In addition, it is also required that the liquid crystal composition is stable to electric field and electromagnetic radiation and the mixed respective liquid crystal compounds are chemically stable under the use environment.

Furthermore, physical values of a refractive index anisotropy ($\Delta n$), a dielectric anisotropy ($\Delta \epsilon$), a viscosity ($\eta$), a conductivity, an elastic constant ratio $K_{33}/K_{11}$ ($K_{33}$: a bend constant, $K_{11}$: a spray elastic constant) and the like of the liquid crystal composition are required to be suitable in compliance with the display system and a device shape. Moreover, it is important that the respective components in the liquid composition have a mutually good solubility.

Among these physical values, a wide liquid crystal phase temperature range, the large dielectric anisotropy, the high elastic constant ratio $K_{33}/K_{11}$ and the like are mainly required for the liquid crystal compounds which can be used in the TFT type display system. In this display system, the improvement of contrast is necessary with the progress of the coloring of the display particularly in recent years. In order to improve the contrast, it is necessary and essential that the liquid crystal compounds have the large refractive index anisotropy value. Furthermore, it is also necessary to lower the dependence of a temperature on a voltage retention. The voltage retention of the liquid crystal compounds is liable to lower with the rise of the temperature. With regard to the displays which have now been used, a back light irradiation type is more prevalent than a reflective type, and in this back light irradiation type, an environment under which a display panel is arranged has a higher temperature than room temperature owing to the irradiation heat of a back light. Under such circumstances, the temperature rise of the liquid crystal compounds is not avoidable. With the temperature rise of the liquid crystal compounds, their voltage retention lowers, and for example, in a normally white mode, a contrast change of from black to white takes place. In consequence, a sharp screen display is impossible.

Many liquid crystal compounds having the low dependence of the temperature on the voltage retention have been heretofore developed. As the suitable compounds, there are well known to a person skilled in the art, for example, compounds having a 3,4,5-trifluorophenyl group which are represented by the following formula (a) and which are mentioned in Japanese Patent Application Laid-open No. 233626/1990. By using any of these compounds as the components of the liquid crystal composition, it is possible to obtain the high voltage retention. However, for the liquid crystal compounds which can be used for the high-speed screen display of a dynamic image or the like, there have been required the expansion of a liquid crystal phase temperature range, the deterioration of viscosity, and a high mutual solubility of the liquid crystal compounds at a low temperature in the case that they are used as the components of the liquid crystal composition.

(a)

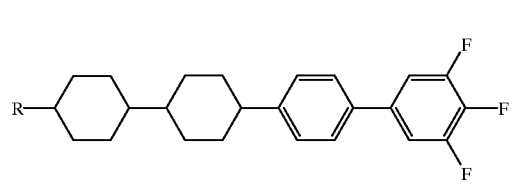

DISCLOSURE OF THE INVENTION

The present invention has been intended to solve the problems of conventional techniques, and an object of the present invention is to provide a liquid crystal compound having a particularly wide liquid crystal phase temperature range, a low viscosity, an improved dependence of a temperature on a voltage retention and an improved solubility at a low temperature, a liquid crystal composition containing this liquid crystal compound, and a liquid crystal display device constituted by the use of the liquid crystal composition.

The present inventors have intensively researched on a compound which can solve the problems, and as a result, it has been found that a liquid crystal compound having a butylene group and/or a propyleneoxy group and a 3,4-difluorophenyl group and having 4 rings in all in one molecule possesses a wide liquid crystal phase temperature range, a low viscosity, a low dependence of a temperature on a voltage retention and a high solubility at a low temperature. Thus, the present inventors have completed the present invention on the basis of this knowledge.

The aspects of the present invention are as follows.

[1] A difluorophenyl derivative compound represented by the general formula (1):

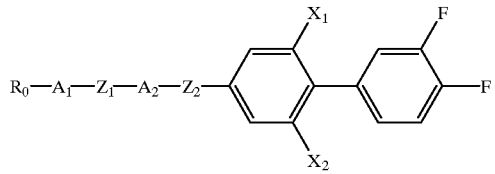

(1)

wherein $R_0$ is an alkyl group or an alkenyl group having 1 to 15 carbon atoms, and an optional methylene group (—$CH_2$—) in the alkyl group or the alkenyl group may be substituted by an oxygen atom (—O—), but 2 or more methylene groups are not continuously substituted by the oxygen atoms; $A_1$ and $A_2$ are each independently a trans-1,4-cyclohexylene group, or one group selected from the group consisting of a 1,4-phenylene group, a pyrimidine-2,5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl in which one or more hydrogen atoms on a six-membered ring may be substituted by halogen atoms; $Z_1$ and $Z_2$ are each independently —$(CH_2)_4$—, —$(CH_2)_3O$—, —$O(CH_2)_3$— or a single bond; $X_1$ and $X_2$ are each independently H, F, Cl or Br; and each of the elements constituting the above compound may be substituted by its isotope.

[2] The difluorophenyl derivative compound according to the above paragraph [1] wherein $Z_1$ is —$(CH_2)_4$— or —$(CH_2)_3O$—; $Z_2$ is a single bond; $A_1$ is a trans-1,4-cyclohexylene group; $A_2$ is a trans-1,4-cyclohexylene group or a 1,4-phenylene group; and $X_1$ and $X_2$ are each a hydrogen atom.

[3] The difluorophenyl derivative compound according to the above paragraph [1] wherein $Z_1$ is —$(CH_2)_4$— or —$(CH_2)_3O$—; $Z_2$ is a single bond; $A_1$ is a trans-1,4-cyclohexylene group; $A_2$ is a trans-1,4-cyclohexylene group or a 1,4-phenylene group; and $X_1$ and/or $X_2$ is a fluorine atom.

[4] The difluorophenyl derivative compound according to the above paragraph [1] wherein $Z_1$ is a single bond; $Z_2$ is —$(CH_2)_4$— or —$(CH_2)_3O$—; $A_1$ is a trans-1,4-cyclohexylene group; $A_2$ is a trans-1,4-cyclohexylene group or a 1,4-phenylene group; and $X_1$ and $X_2$ are each a hydrogen atom.

[5] The difluorophenyl derivative compound according to the above paragraph [1] wherein $Z_1$ is a single bond; $Z_2$ is —$(CH_2)_4$— or —$(CH_2)_3O$—; $A_1$ is a trans-1,4-cyclohexylene group; $A_2$ is a trans-1,4-cyclohexylene group or a 1,4-phenylene group; and $X_1$ and/or $X_2$ is a fluorine atom.

[6] A liquid crystal composition which comprises 2 or more components containing at least one difluorophenyl derivative compound described in any one of the above paragraphs [1] to [5].

[7] A liquid crystal composition which comprises at least one difluorophenyl derivative compound described in any one of the above paragraphs [1] to [5] as a first component, and at least one compound selected from the group consisting of the general formulae (2), (3) and (4) as a second component:

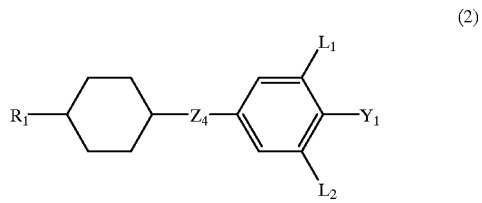

(2)

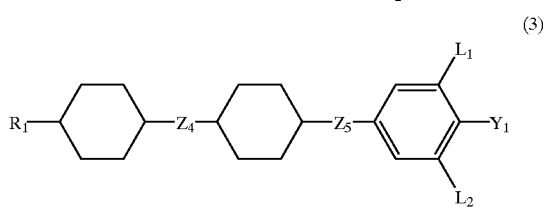

(3)

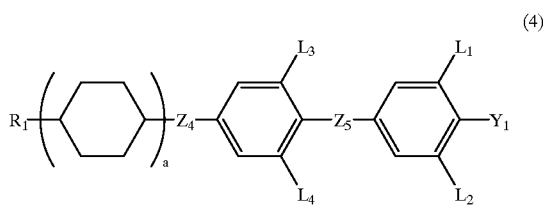

(4)

wherein $R_1$ is an alkyl group having 1 to 10 carbon atoms; $Y_1$ is F, Cl, $OCF_3$, $OCF_2H$, $CF_3$, $CF_2H$ or $CFH_2$; and $L_1$, $L_2$, $L_3$ and $L_4$ are each independently H or F; $Z_4$ and $Z_5$ are each independently —$(CH_2)_2$—, —CH=CH— or a single bond; and a is 1 or 2.

[8] A liquid crystal composition which comprises at least one difluorophenyl derivative compound described in any one of the above paragraphs [1] to [5] as a first component, and at least one compound selected from the group consisting of the general formulae (5), (6), (7), (8) and (9) as a second component:

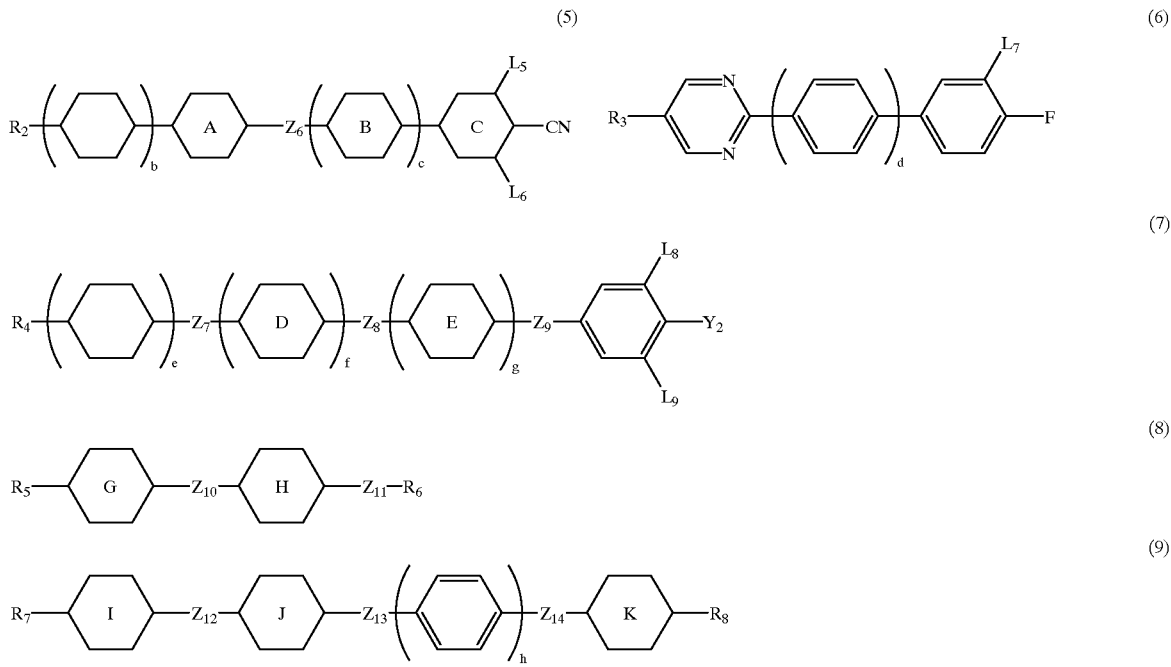

in the general formula (5), $R_2$ is F, an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring A is a trans-1,4-cyclohexylene group, a 1,4-phenylene group, a pyrimidine-2,5-diyl group or a 1,3-dioxane-2,5-diyl group; a ring B is a trans-1,4-cyclohexylene group, a 1,4-phenylene group or a pyrimidine-2,5-diyl group; a ring C is a trans-1,4-cyclohexylene group or a 1,4-phenylene group; $Z_6$ is —$(CH_2)_2$—, —COO— or a single bond; $L_5$ and $L_6$ are each independently H or F; and b and c are each independently 0 or 1, in the general formula (6), $R_3$ is an alkyl group having 1 to 10 carbon atoms; $L_7$ is H or F; and d is 0 or 1, in the general formula (7), $R_4$ is an alkyl group having 1 to 10 carbon atoms; a ring D and a ring E are each independently a trans-1,4-cyclohexylene group or a 1,4-phenylene group; $Z_7$ and $Z_8$ are each independently —COO— or a single bond; $Z_9$ is —COO— or —C≡C—; $L_8$ and $L_9$ are each independently H or F; $Y_2$ is F, $OCF_3$, $OCF_2H$, $CF_3$, $CF_2H$ or $CFH_2$; and e, f and g are each independently 0 or 1, in the general formula (8), $R_5$ and $R_6$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring G is a trans-1,4-cyclohexylene group, a 1,4-phenylene group or a pyrimidine-2,5-diyl group; a ring H is a trans-1,4-cyclohexylene group or a 1,4-phenylene group; $Z_{10}$ is —C≡C—, —COO—, —$(CH_2)_2$—, —CH=CH—C≡C— or a single bond; and $Z_{11}$ is —COO— or a single bond, and in the general formula (9), $R_7$ and $R_8$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring I is a trans-1,4-cyclohexylene group, a 1,4-phenylene group or a pyrimidine-2,5-diyl group; a ring J is a trans-1,4-cyclohexylene group or a 1,4-phenylene group in which one or more hydrogen atoms on the ring may be substituted by F, or a pyrimidine-2,5-diyl group; a ring K is a trans-1,4-cyclohexylene group or a 1,4-phenylene group; $Z_{12}$ and $Z_{14}$ are each independently —COO—, —$(CH_2)_2$— or a single bond; $Z_{13}$ is —CH=CH—, —C≡C—, —COO— or a single bond; and h is 0 or 1.

[9] A liquid crystal composition which comprises at least one liquid crystal compound described in any one of the above paragraphs [1] to [5] as a first component, at least one compound selected from the group consisting of the general formulae (2), (3) and (4) as a part of a second component, and at least one compound selected from the group consisting of the general formulae (5), (6), (7), (8) and (9) as the other part of the second component.

[10] A liquid crystal display device which is constituted by using a liquid crystal composition described in any one of the above paragraphs [6] to [9].

The compound of the present invention is physically and chemically extremely stable under conditions under which the liquid crystal device is used, and has a wide liquid crystal phase temperature range, a high solubility in the liquid crystal composition even at a low temperature, a low viscosity, a low dependence of a temperature on a voltage retention and a large pretilt angle. In addition, the desired physical values of the compound can be optionally regulated by suitably selecting a ring structure, a bond group or a side chain structure of its molecule. Therefore, in the case that the compound of the present invention is used as the component for the liquid crystal composition, the liquid composition having the above good characteristics can be obtained. Moreover, in the case that the liquid crystal composition containing the compound of the present invention as a constitutional component is used for the liquid crystal display device, the obtained liquid crystal display device is stable to an external environment and drivable at a low voltage, and has a wide use temperature range, a high-speed response and a high contrast. In particular, the compound of the present invention is extremely excellent as a constitutional component of the nematic liquid crystal composition for use in a TFT type display system.

BEST MODE FOR CARRYING OUT THE INVENTION

Each difluorophenyl derivative compound represented by the general formula (1) of the present invention exhibits suitable physical properties as a liquid crystal material. By using a compound in which $A_1$, $A_2$, $Z_1$, $Z_2$, $X_1$ and $X_2$ in the general formula (1) are suitably selected, a liquid crystal composition suitable for a use purpose can be prepared.

That is to say, if a large refractive index anisotropy value is necessary, a compound in which $A_2$ is a 1,4-phenylene group and $Z_1$ or $Z_2$ is a single bond should be selected. Furthermore, a compound in which a hydrogen atom of the 1,4-phenylene group is replaced with a fluorine atom exhibits a particularly excellent solubility at a low temperature.

In particular, the compounds of the general formula (1) which are preferable as liquid crystal materials can be represented by the following formulae (1-1) to (1-18):

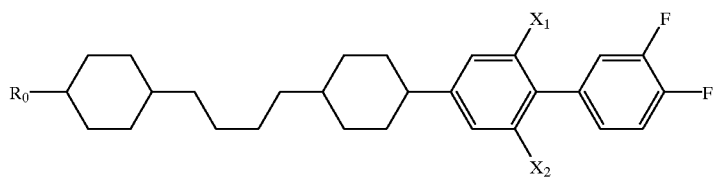
(1-1)

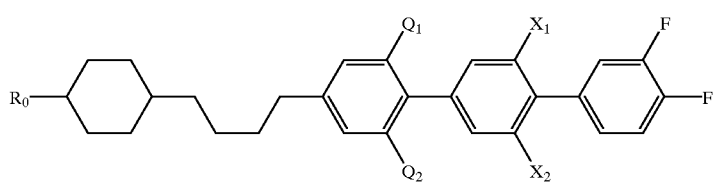
(1-2)

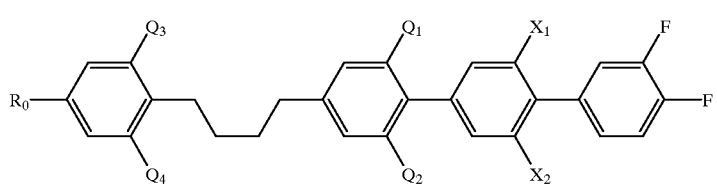
(1-3)

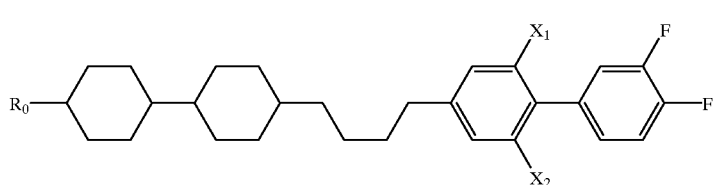
(1-4)

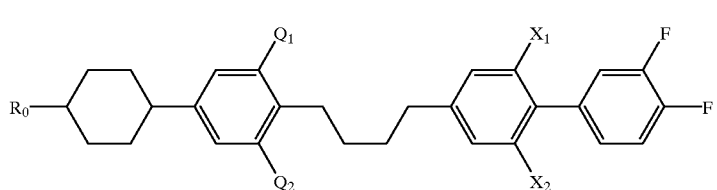
(1-5)

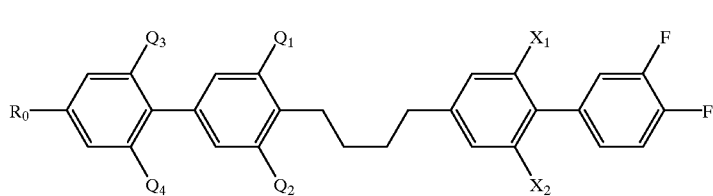
(1-6)

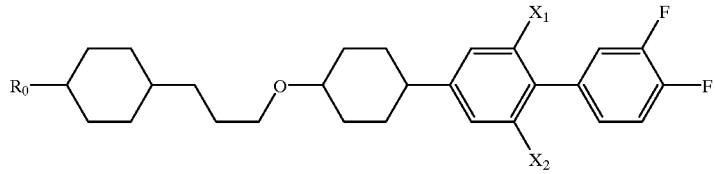
(1-7)
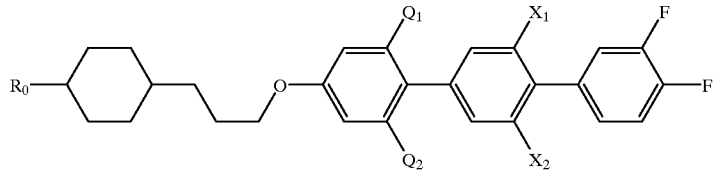
(1-8)
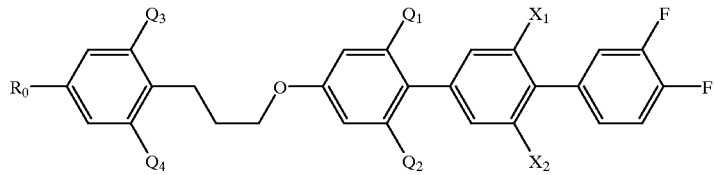
(1-9)
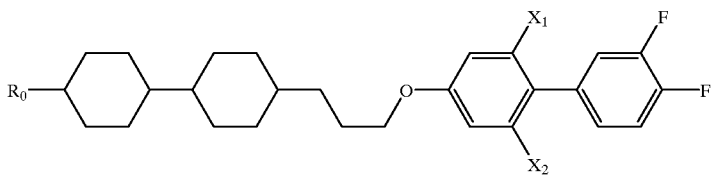
(1-10)
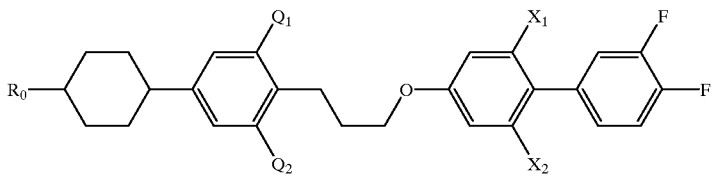
(1-11)
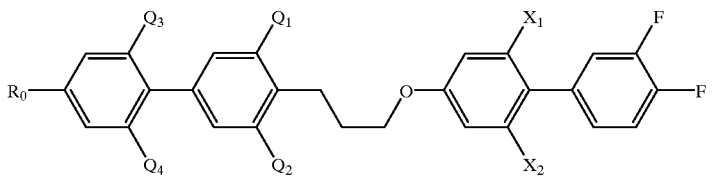
(1-12)
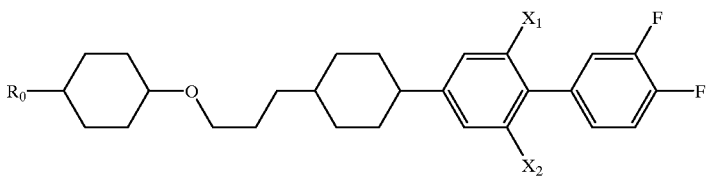
(1-13)
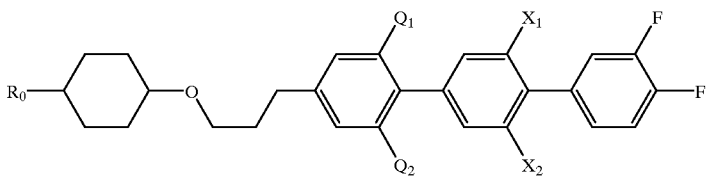
(1-14)

(1-15)

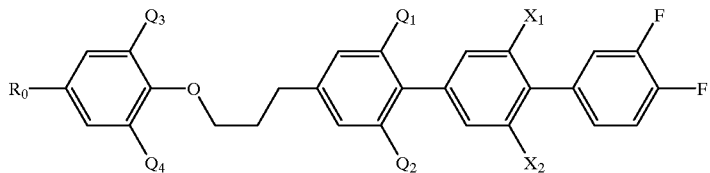

(1-16)

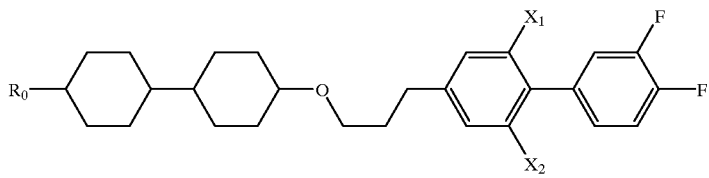

(1-17)

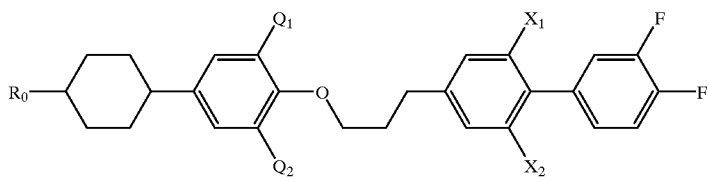

(1-18)

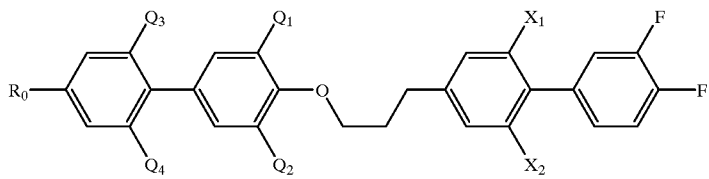

In the formulae (1-1) to (1-18), $R_0$, $X_1$ and $X_2$ are as defined above, and $Q_1$, $Q_2$, $Q_3$ and $Q_4$ are each independently a hydrogen atom or a halogen atom, and each of the elements constituting each compound may be substituted by its isotope. $R_0$ in the formulae (1-1) to (1-18) is preferably an alkyl group, an alkoxy group, an alkoxyalkyl group, an alkenyl group, an alkenyloxy group, an alkenyloxyalkyl group or an alkyloxyalkenyl group having 1 to 12 carbon atoms, and particularly preferable examples thereof include methyl, ethyl, propyl, butyl, pentyl, hexyl, heptyl, octyl, methoxy, ethoxy, propoxy, butoxy, pentyloxy, hexyloxy, heptyloxy, octyloxy, methoxymethyl, ethoxymethyl, propoxymethyl, butoxymethyl, methoxyethyl, ethoxyethyl, propoxyethyl, methoxypropyl, ethoxypropyl, propoxypropyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 4-pentinyloxy, methoxy-1-propenyl, methoxy-1-pentenyl and methoxy-3-pentenyl.

By using the first component alone containing at least one of the compounds represented by the formula (1), the liquid crystal composition having good characteristics can be obtained. However, a more preferable liquid crystal composition can be obtained by mixing the above first component, at least one compound (hereinafter referred to as "the second A component") selected from the group consisting of the general formulae (2), (3) and (4) and/or at least one compound (hereinafter referred to as "the second B component") selected from the group consisting of the general formulae (5), (6), (7), (8) and (9). In order to express the good characteristics, a mixing ratio of the compound represented by the general formula (1) is preferably in the range of 0.1 to 99.9% by weight.

For the purpose of regulating a threshold voltage, a liquid crystal temperature region, a refractive index anisotropy value, a dielectric anisotropy value, a viscosity and the like, a known compound can be mixed as a third component.

Preferable examples of the second A components represented by the general formulae (2), (3) and (4) include compounds represented by the formulae (2-1) to (2-15), (3-1) to (3-48), and (4-1)–(4-55):

(2-1)

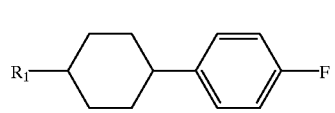

(2-2)

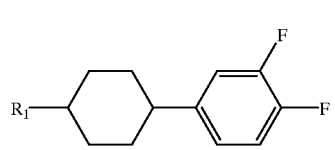

(2-3)

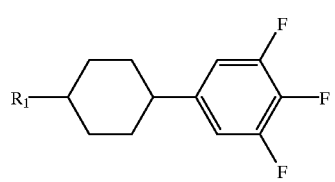

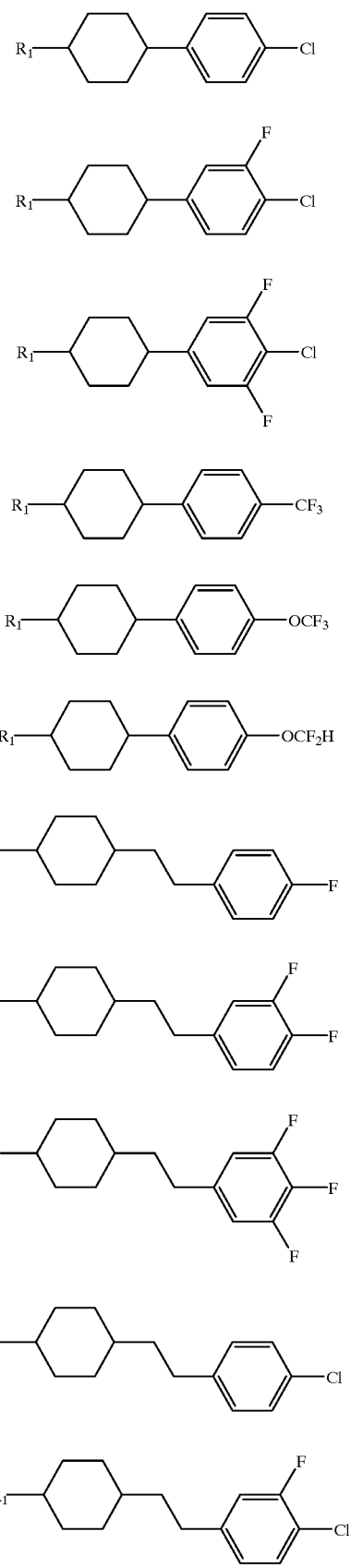
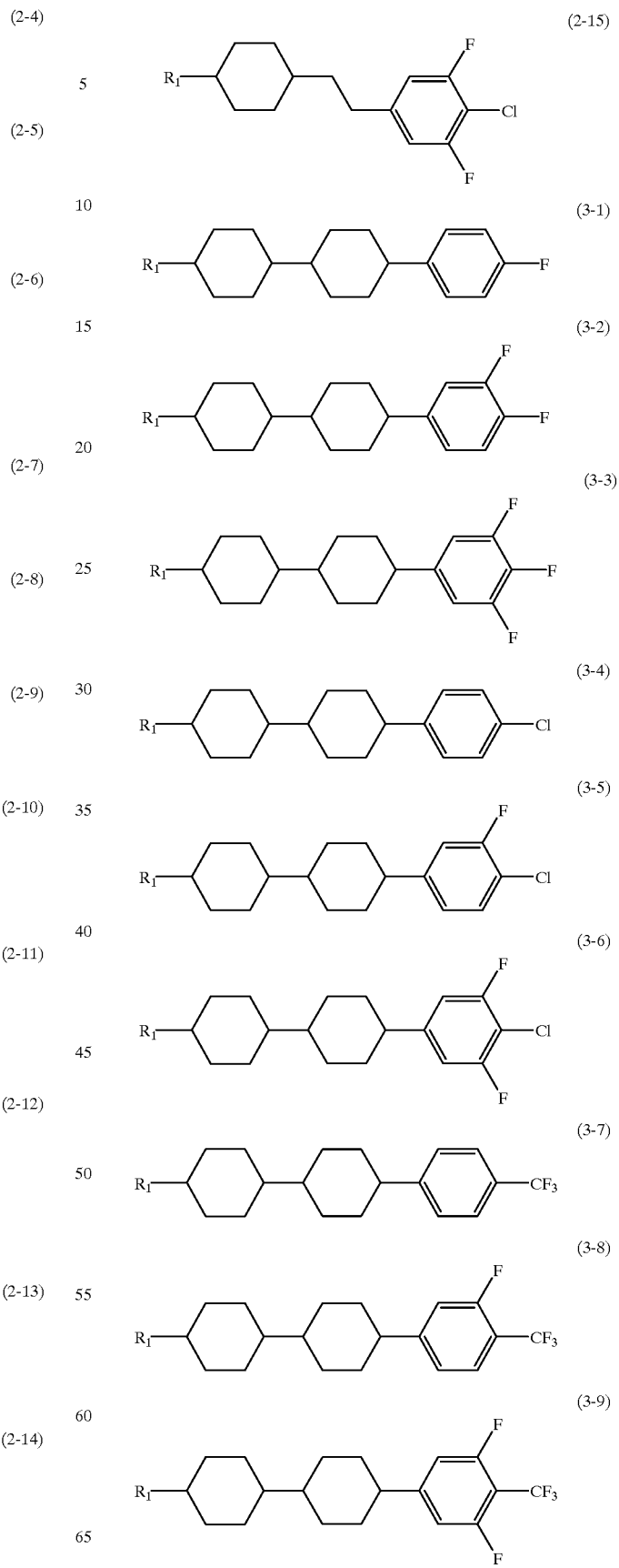

(3-10) 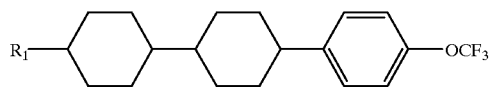
(3-11) 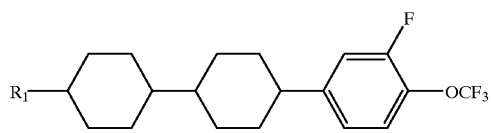
(3-12) 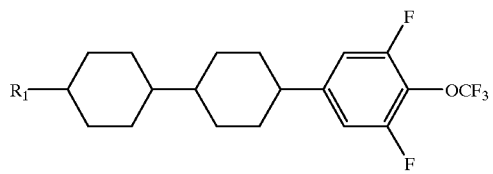
(3-13) 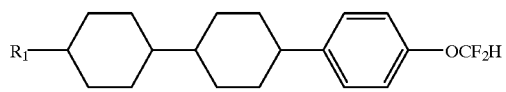
(3-14) 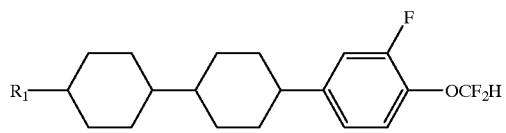
(3-15) 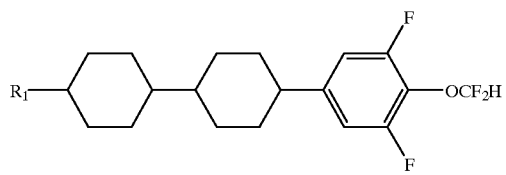
(3-16) 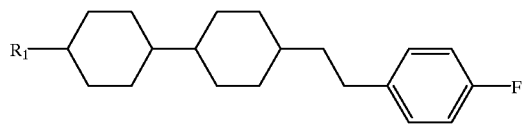
(3-17) 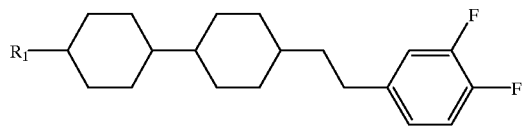
(3-18) 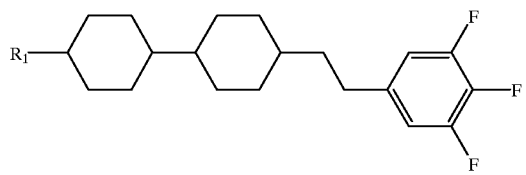
(3-19) 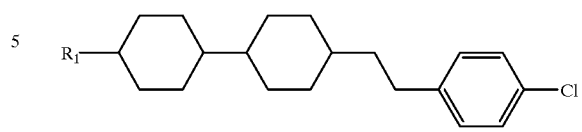
(3-20) 
(3-21) 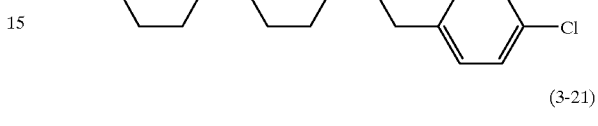
(3-22) 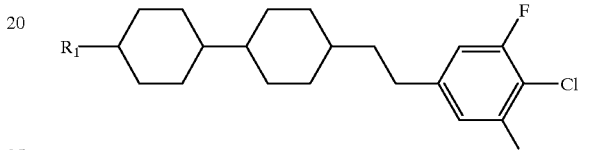
(3-23) 
(3-24) 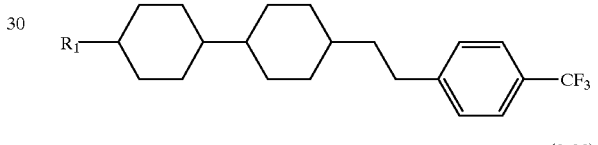
(3-25) 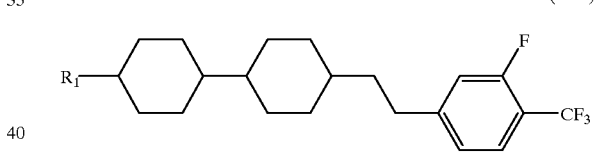
(3-26) 

(3-27)
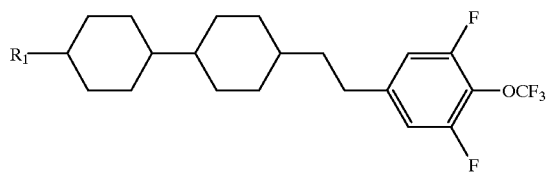
(3-28)
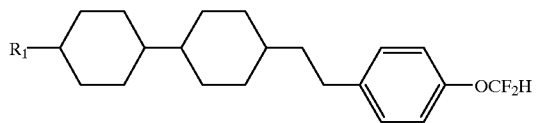
(3-29)
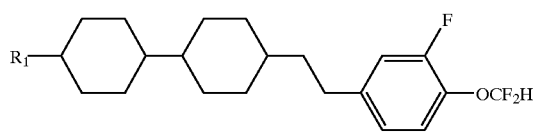
(3-30)
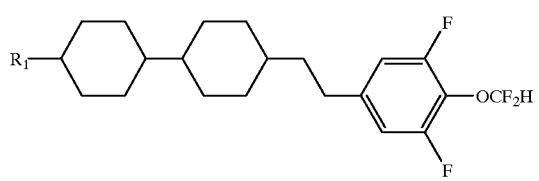
(3-31)
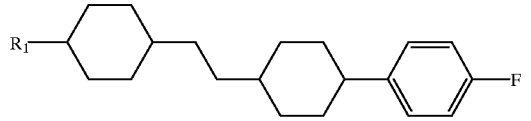
(3-32)
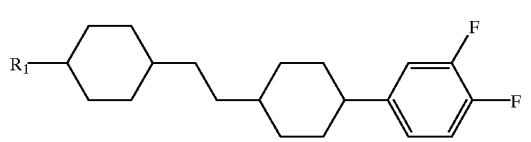
(3-33)
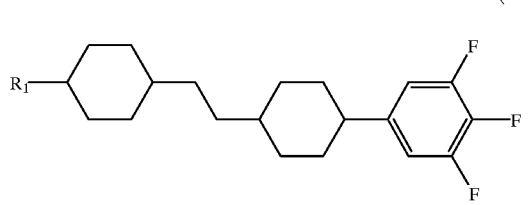
(3-34)
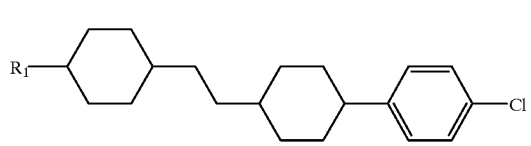
(3-35)
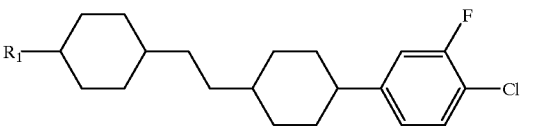
(3-36)
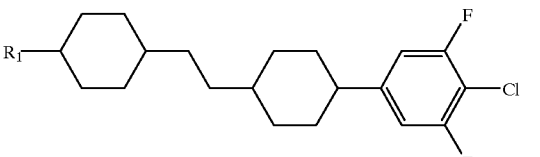
(3-37)
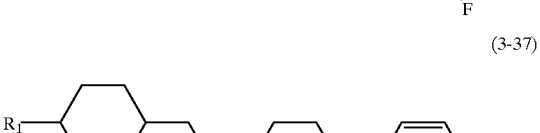
(3-38)
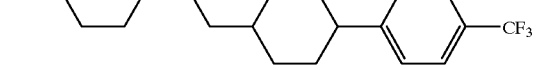
(3-39)
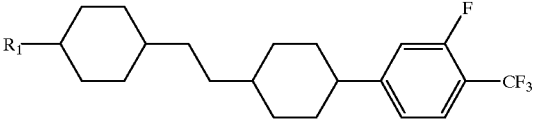
(3-40)
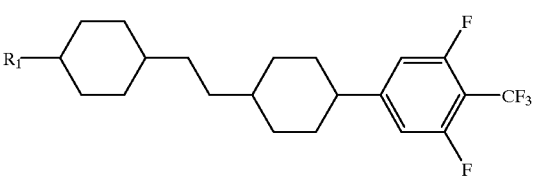
(3-41)
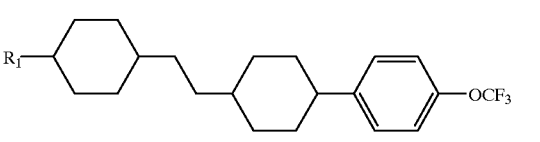
(3-42)
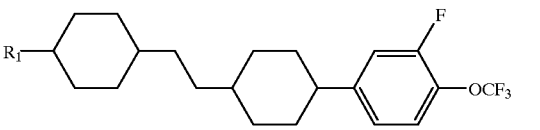

(3-43) 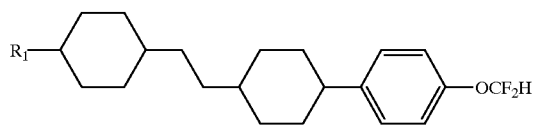
(3-44) 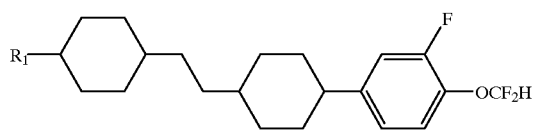
(3-45) 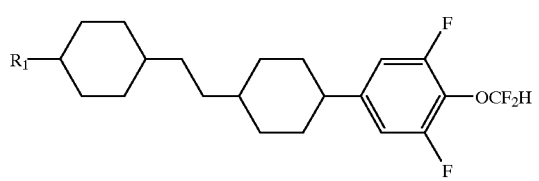
(3-46) 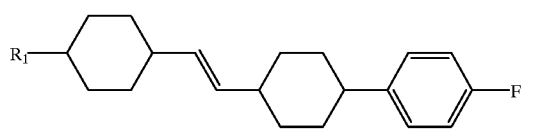
(3-47) 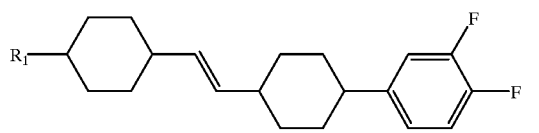
(3-48) 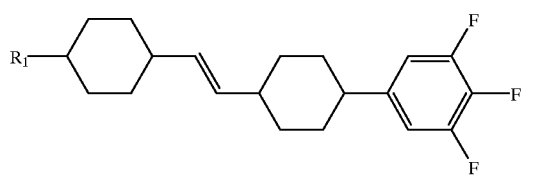
(4-1) 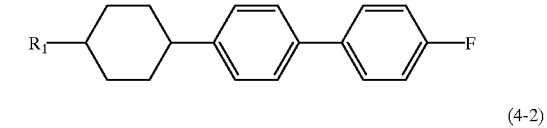
(4-2) 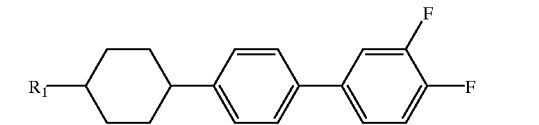
(4-3) 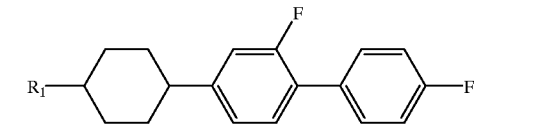
(4-4) 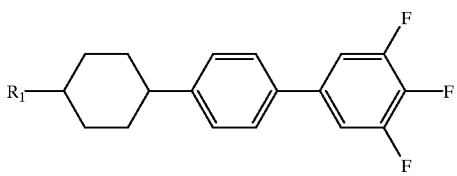
(4-5) 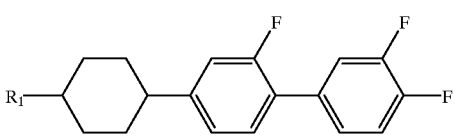
(4-6) 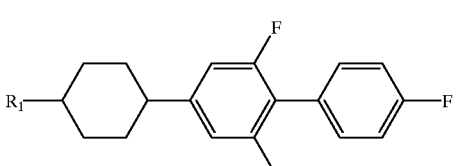
(4-7) 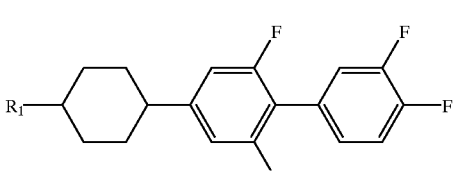
(4-8) 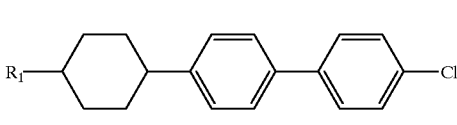
(4-9) 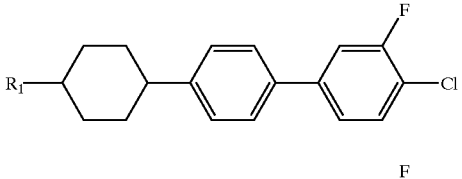
(4-10) 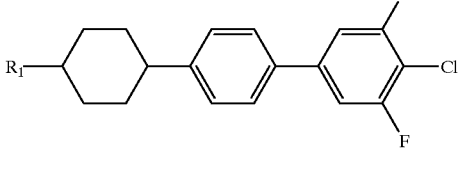
(4-11) 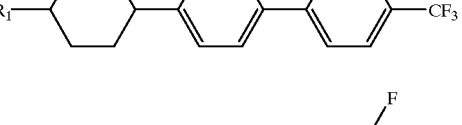
(4-12) 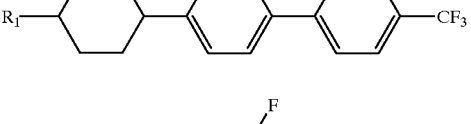
(4-13) 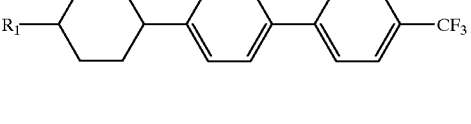

(4-14) 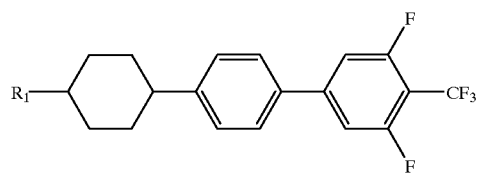
(4-15) 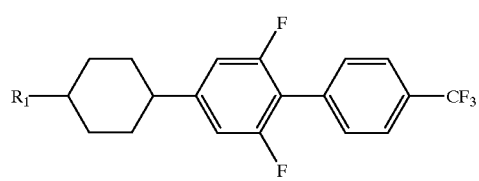
(4-16) 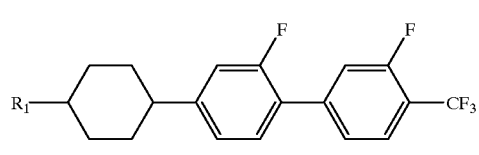
(4-17) 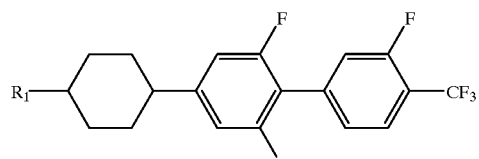
(4-18) 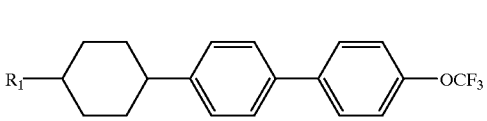
(4-19) 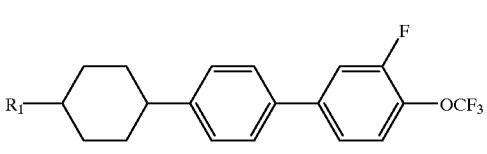
(4-20) 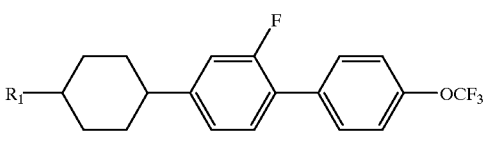
(4-21) 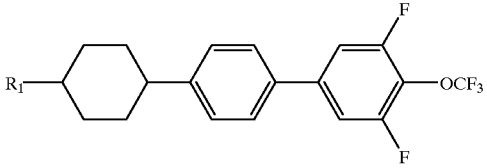
(4-22) 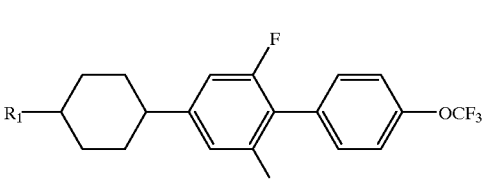
(4-23) 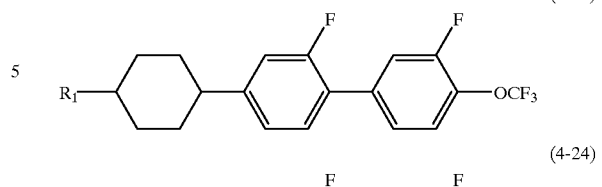
(4-24) 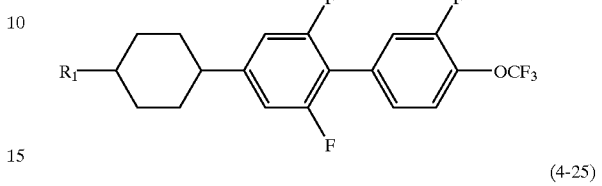
(4-25) 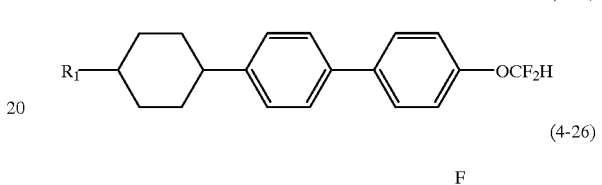
(4-26) 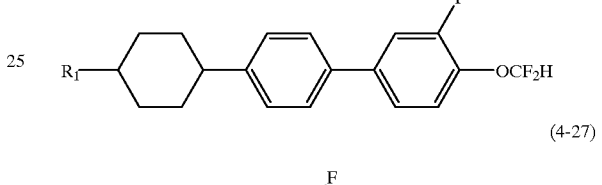
(4-27) 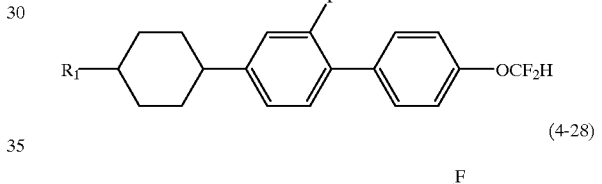
(4-28) 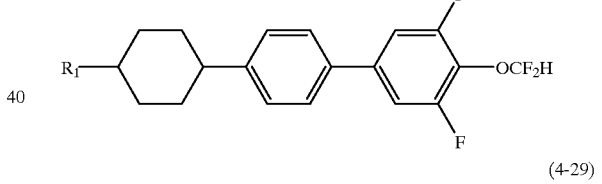
(4-29) 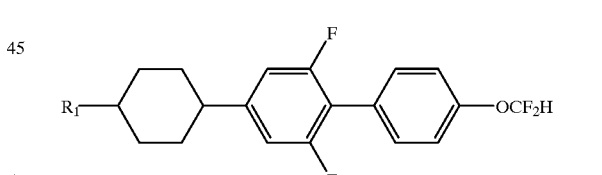
(4-30) 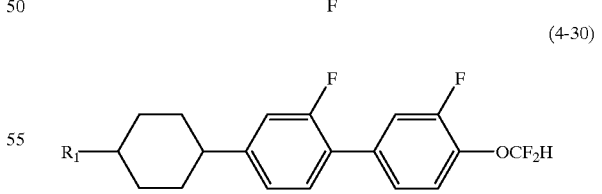
(4-31) 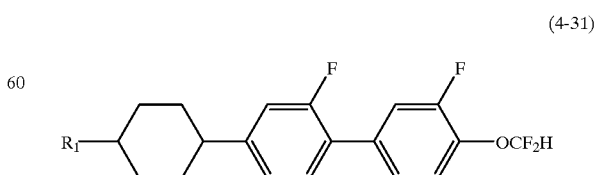

-continued

-continued

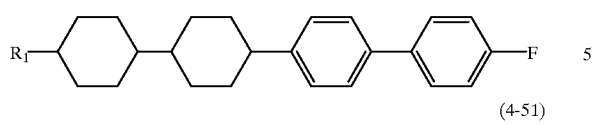
(4-50)

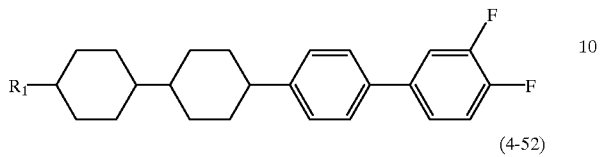
(4-51)

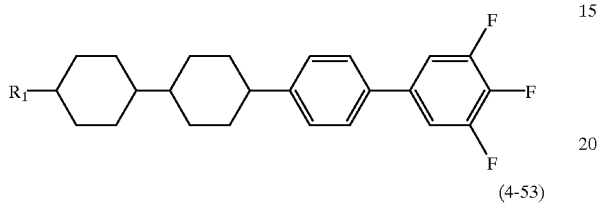
(4-52)

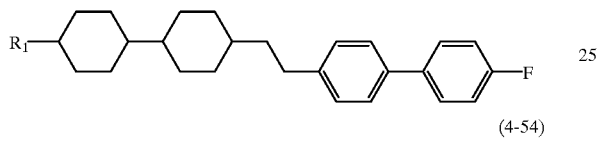
(4-53)

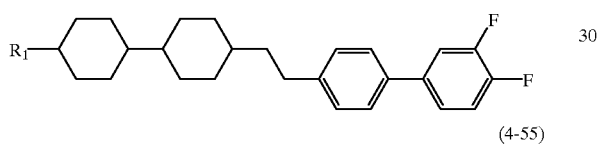
(4-54)

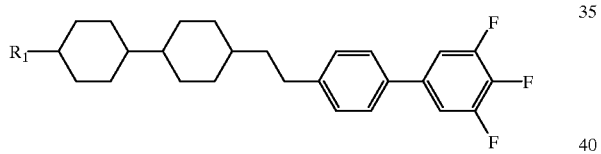
(4-55)

In the above formulae, $R_1$ is as defined above.

The compounds represented by these general formulae (2) to (4) have positive dielectric anisotropy values and are very excellent in heat stability and chemical stability.

The amount of the compound to be used is usually in the range of 1 to 99% by weight, preferably 10 to 97% by weight, more preferably 40 to 95% by weight, with respect to the total weight of the liquid crystal composition.

Preferable examples of the second B components represented by the general formulae (5), (6) and (7) include compounds represented by the formulae (5-1) to (5-24), (6-1) to (6-3), and (7-1)–(7-28):

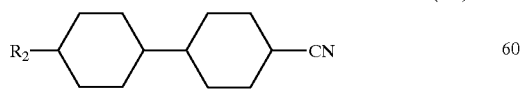
(5-1)

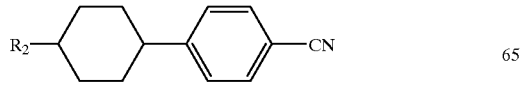
(5-2)

-continued

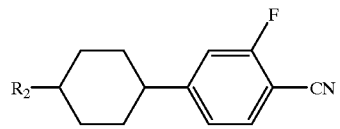
(5-3)

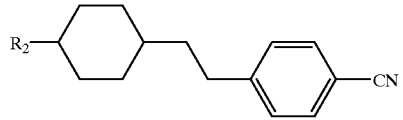
(5-4)

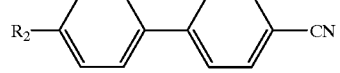
(5-5)

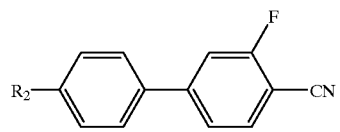
(5-6)

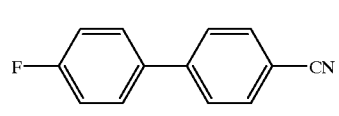
(5-7)

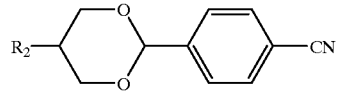
(5-8)

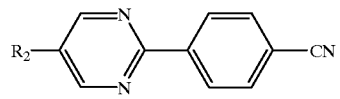
(5-9)

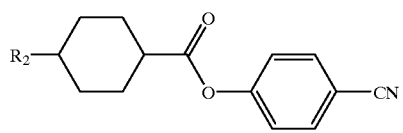
(5-10)

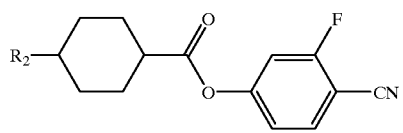
(5-11)

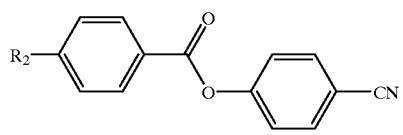
(5-12)

(5-13)

(5-14)
(5-15)
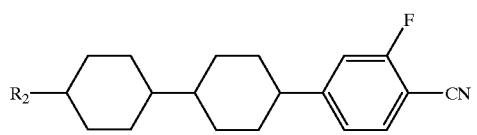
(5-16)
(5-17)
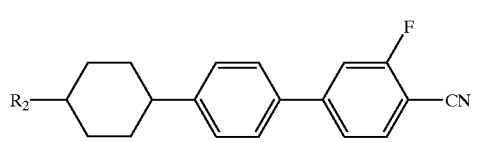
(5-18)
(5-19)
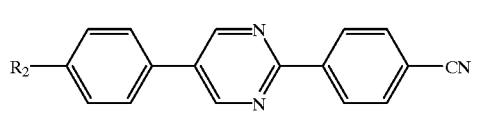
(5-20)
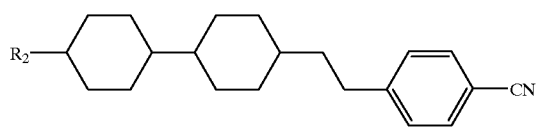
(5-21)
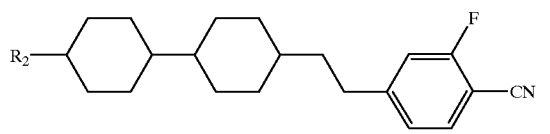
(5-22)
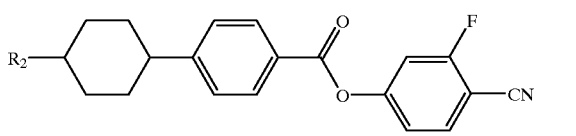
(5-23)
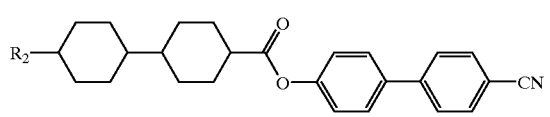
(5-24)
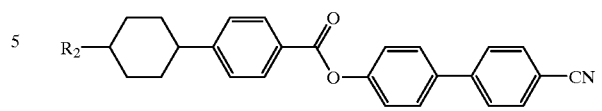
(6-1)
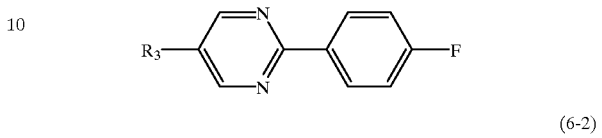
(6-2)
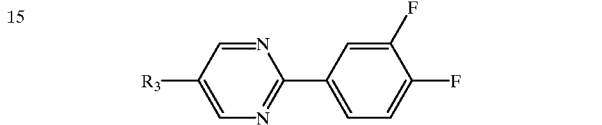
(6-3)
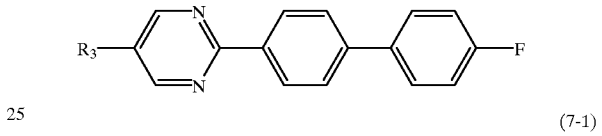
(7-1)
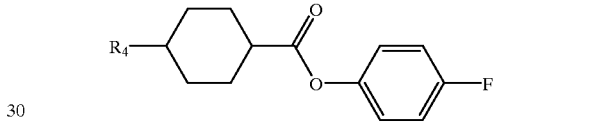
(7-2)
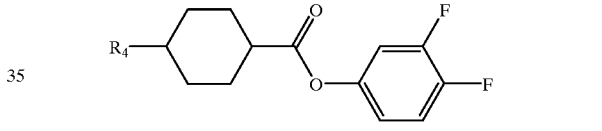
(7-3)
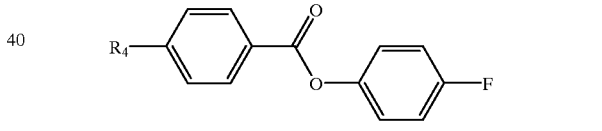
(7-4)
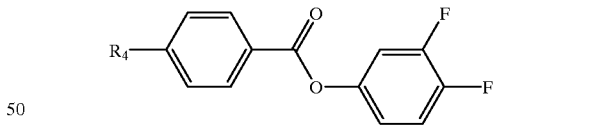
(7-5)
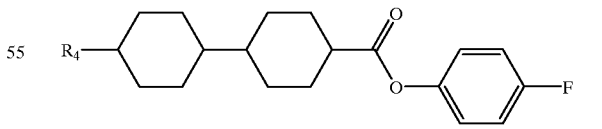
(7-6)
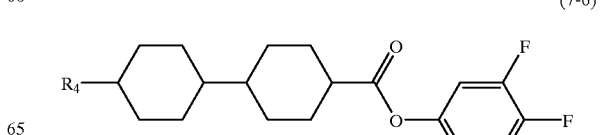

(7-7)
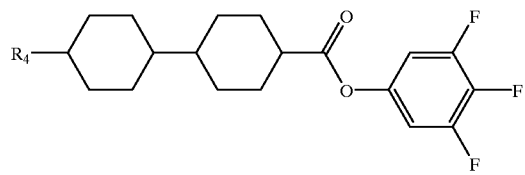
(7-8)
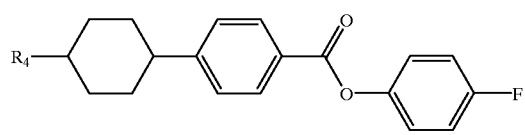
(7-9)
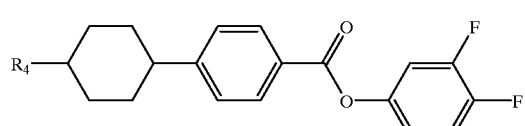
(7-10)
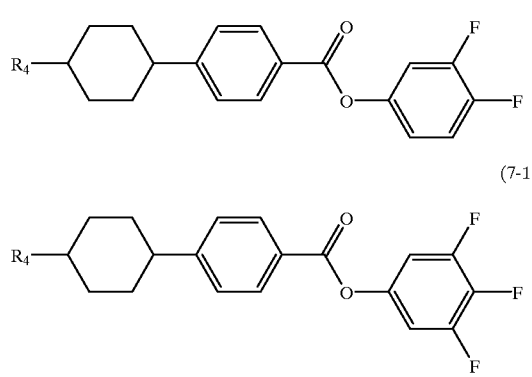
(7-11)
(7-12)
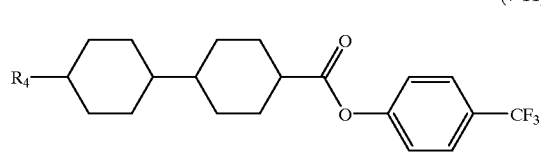
(7-13)
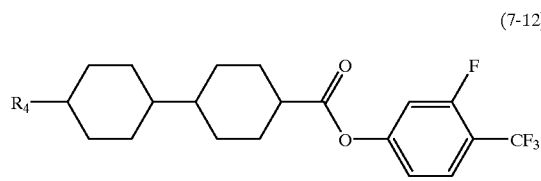
(7-14)
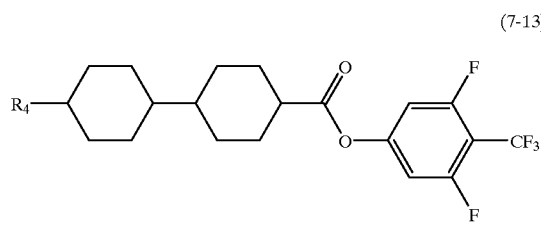
(7-15)
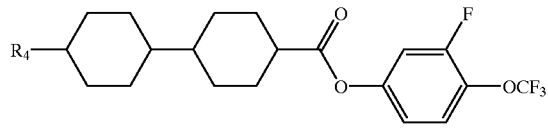
(7-16)
(7-17)
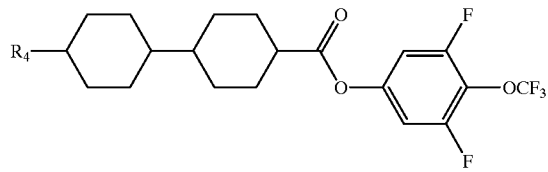
(7-18)
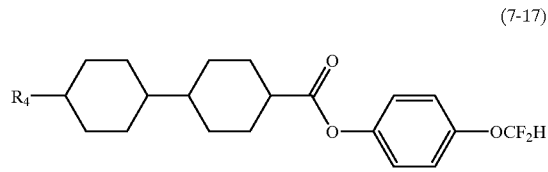
(7-19)
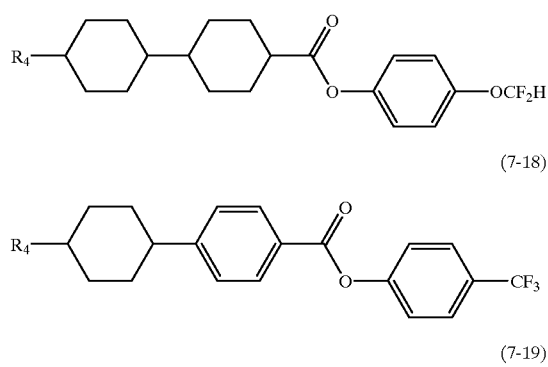
(7-20)
(7-21)
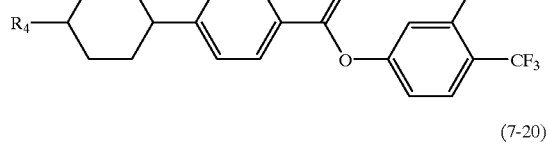
(7-22)
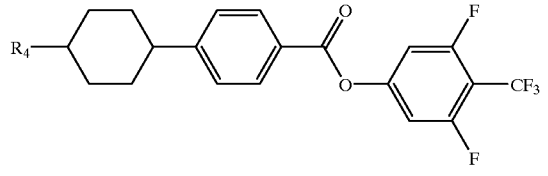
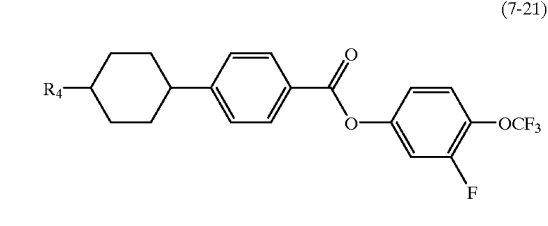
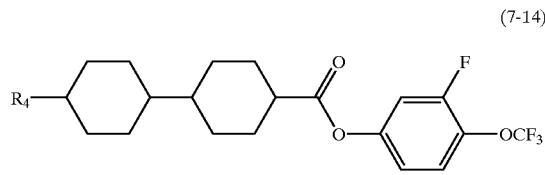
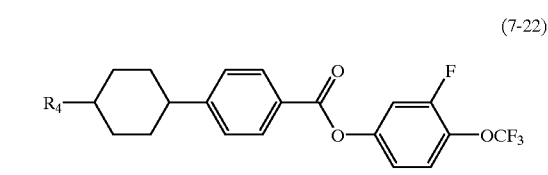

-continued (7-23)
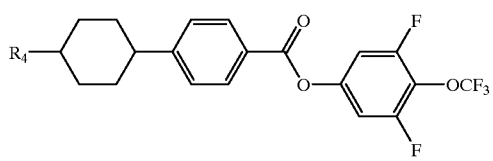

(7-24)
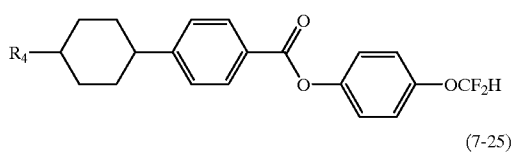

(7-25)
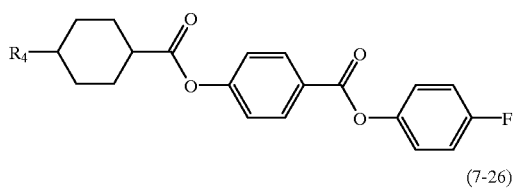

(7-26)
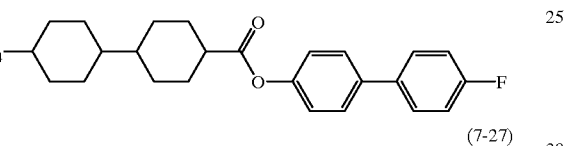

(7-27)
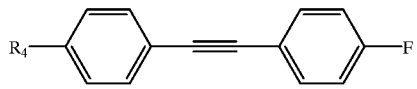

(7-28)
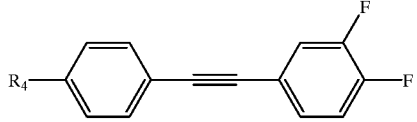

In the above formulae, $R_2$, $R_3$ and $R_4$ are as defined above.

The compounds represented by these general formulae (5) to (7) have positive and large dielectric anisotropy values. These compounds can each be added as the component for the liquid crystal composition, and they can be particularly used for the purpose of reducing the threshold voltage of the liquid crystal composition. In addition, these compounds can also be used for the purposes of the regulation of the viscosity and the refractive index anisotropy value, the expansion of the liquid crystal temperature region, and the improvement of a steepness of electrooptic characteristics.

Preferable examples of the second B components represented by the general formulae (8) and (9) include compounds represented by the formulae (8-1) to (8-8) and (9-1) to (9-13):

(8-1)
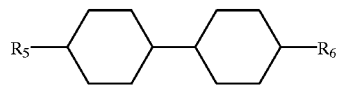

(8-2)
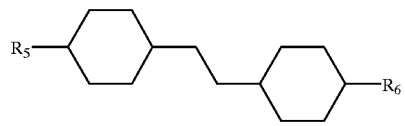

(8-3)
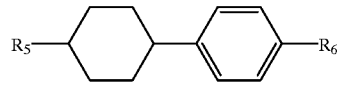

(8-4)
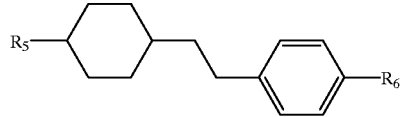

(8-5)
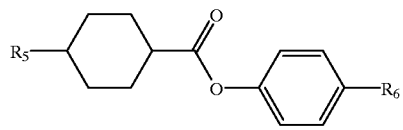

(8-6)
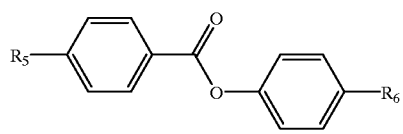

(8-7)
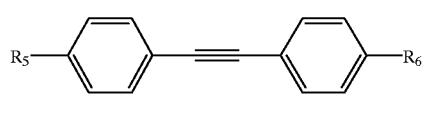

(8-8)
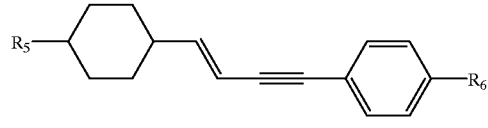

(9-1)
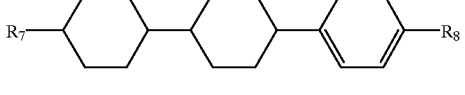

(9-2)
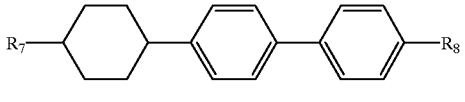

(9-3)
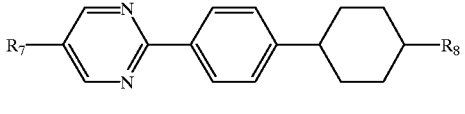

(9-4)
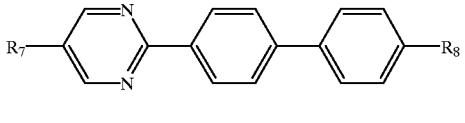

(9-5)
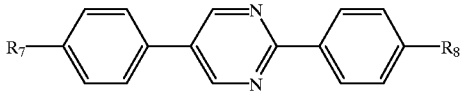

-continued

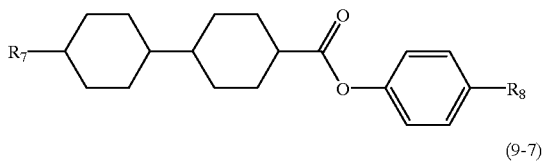
(9-6)

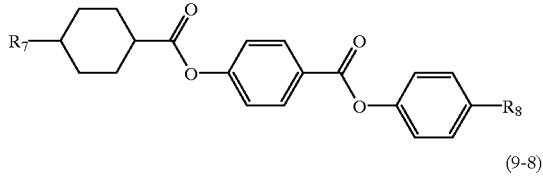
(9-7)

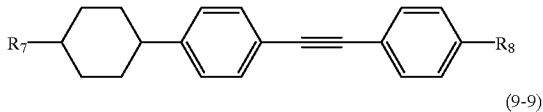
(9-8)

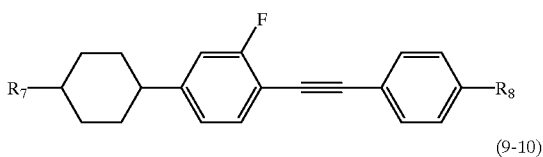
(9-9)

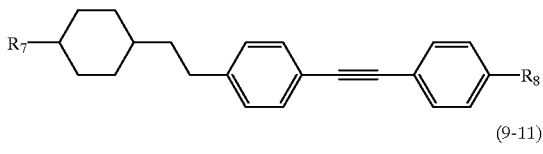
(9-10)

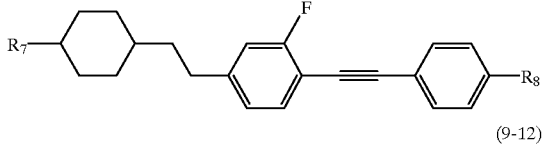
(9-11)

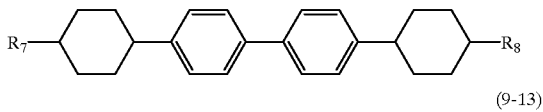
(9-12)

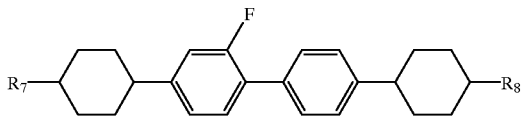
(9-13)

In the above formulae, $R_5$ and $R_6$ are as defined above.

The compounds represented by these general formulae (8) and (9) have negative or small dielectric anisotropy values. Each of the compounds represented by the general formula (8) can mainly be added to the liquid crystal composition for the purpose of decreasing the viscosity and/or regulating the refractive index anisotropy value of the liquid crystal composition. In addition, each of the compounds represented by the general formula (9) can be added for the purpose of expanding a nematic range to heighten a transparent point and/or regulating the refractive index anisotropy value.

By the use of the compounds represented by the general formulae (5) to (9), the liquid crystal composition which is particularly suitable for an STN display system and a usual TN display system can be prepared.

The amount of the compounds represented by the general formulae (5) to (9) is usually in the range of 1 to 99% by weight, preferably 10 to 97% by weight, more preferably 40 to 95% by weight, in the case that the liquid crystal composition for the usual TN display system and STN display system is prepared. In this case, any of the compounds represented by the general formulae (2) and (4) may be partially used.

The liquid crystal composition regarding the present invention can be used for the TFT liquid crystal display device, whereby the steepness of the electrooptic characteristics and a viewing angle can be improved. Furthermore, since the compound represented by the general formula (1) has a low viscosity, the response velocity of the liquid crystal display device using this compound can be improved, and hence it is extremely high.

The liquid crystal composition itself of the present invention can be prepared in a conventional manner. In general, there is employed a method in which the various liquid crystal components are mutually dissolved at a high temperature. However, there may be employed a method which comprises dissolving the liquid crystal components in an organic solvent, mixing them, and then distilling off the solvent under reduced pressure.

Furthermore, the liquid crystal composition of the present invention can be improved and optimized in compliance with an intended use by adding suitable additives. Such additives are well known by a person skilled in the art and described in detail in literature and the like.

Usually, in order to form a spiral structure of the liquid crystal and to thereby regulate a necessary twist angle, a chiral compound can be added.

In addition, the liquid crystal composition of the present invention can be used as the liquid crystal composition for a guest-host (GH) mode by adding a dichromatic dye such as a merocyanine dye, a styryl dye, an azo dye, an azomethine dye, an azoxy dye, a quinophthalone dye, an anthraquinone dye or a tetrazine dye to the liquid crystal composition. Moreover, the liquid crystal composition of the present invention can also be used as the liquid crystal composition for NCAP in which microcapsules containing the nematic liquid crystal are used, and as the liquid crystal composition for a polymer dispersion type liquid crystal display device (PDLCD) typified by a polymer network liquid crystal display device (PNLCD) in which a three-dimensional network polymer is formed in the liquid crystal. In addition, the liquid crystal composition of the present invention can also be used as the liquid crystal composition for an effective controlled birefringent (ECB) mode and a dynamic scattering mode (DS).

The compound represented by the general formula (1) of the present invention can easily be manufactured by using a usual chemical technique of an organic synthesis. For example, by suitably selecting and combining known reactions described in literature and magazines such as Organic Synthesis, Organic Reactions, Shin Zikken Kagaku Koza, the compound represented by the general formula (1) can easily be synthesized.

When the bond group $Z_1$ or $Z_2$ is a butylene group, the compound can be prepared through, for example, the following reaction route.

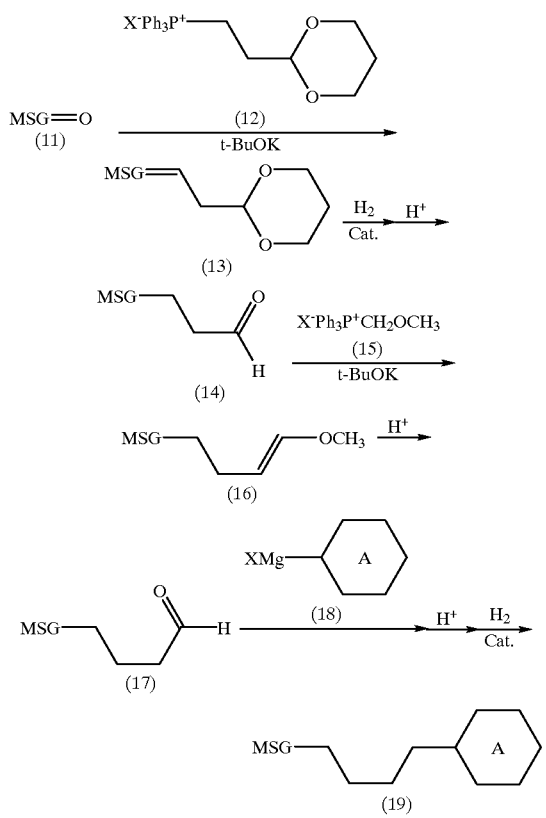

X = Cl, Br, I

However, in the compounds in the formulae (11) to (19) showing the above reaction route, MSG is a mesogen (a residue of an organic compound), and a ring A is one group selected from the group consisting of a trans-1,4-cyclohexylene group, a 1,4-phenylene group in which one or more hydrogen atoms on the six-membered ring may be substituted by halogen atoms, a pyrimidine-2,5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl.

That is to say, 2-(1,3-dioxane-2-yl) ethyltriphenylphosphonium halide 12 and an aldehyde derivative 11 are subjected to a Wittig reaction in the presence of a base such as sodium methylate, potassium-t-butoxide (t-BuOK) or butyl lithium in an ether solvent such as tetrahydrofuran (abbreviated to as "THF") or diethyl ether to obtain a compound 13. Next, the hydrogen reduction of the compound 13 is carried out in the presence of a metal catalyst such as palladium/carbon or a Raney nickel in a mixed solvent of toluene/ethanol, and the thus reduced compound is then reacted with a mineral acid such as hydrochloric acid or sulfuric acid, or an organic acid such as formic acid or p-toluenesulfonic acid to obtain an aldehyde derivative 14. Furthermore, this aldehyde derivative 14 and a compound 15 are subjected to the Wittig reaction in the same manner as in the above preparation of the compound 13 from the aldehyde derivative 11 to obtain a compound 16, and this compound is then reacted with the same acid as mentioned above, thereby preparing an aldehyde derivative 17. Next, this aldehyde derivative 17 is reacted with a Grignard reagent 18 to carry out a Grignard reaction, and the same acid as mentioned above is added to the reaction system to accomplish dehydration. In succession, the hydrogen reduction is done by the use of the same metal catalyst as mentioned above, whereby a derivative 19 having a butylene group can be manufactured.

When the bond group $Z_1$ or $Z_2$ is a propyleneoxy group having an ether bond, the compound represented by the general formula (1) can be prepared through, for example, the following reaction route.

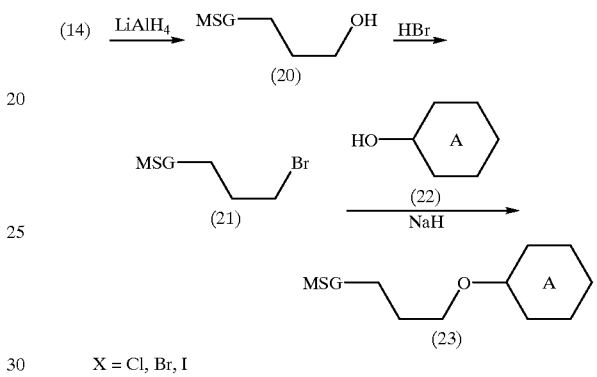

X = Cl, Br, I

In the compounds in the formulae (20) to (23) showing the above reaction route, MSG is a mesogen (a residue of an organic compound), and a ring A is one group selected from the group consisting of a trans-1,4-cyclohexylene group, a 1,4-phenylene group in which one or more hydrogen atoms on the six-membered ring may be substituted by halogen atoms, a pyrimidine-2,5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl.

That is to say, the aldehyde derivative 14 is reacted with lithium aluminum hydride in a solvent such as toluene, THF or diethyl ether to reduce the aldehyde derivative, thereby obtaining an alcohol derivative 20. This alcohol derivative 20 is then reacted with hydrobromic acid to prepare a compound 21. Next, this compound 21 is reacted with a compound 22 in the presence of sodium hydride to prepare a compound 23 having the ether bond.

The above reactions can be suitably selected and carried out, thereby obtaining a compound 24 in the following reaction formula. This compound 24 is reacted with n-butyl lithium and zinc chloride in turn, and it is further reacted with 3,4-difluoro-1-bromobenzene in the presence of a metal catalyst of palladium (0) to accomplished a coupling reaction, whereby the compound represented by the general formula (1) of the present invention can be manufactured. In the following, this reaction route will be shown.

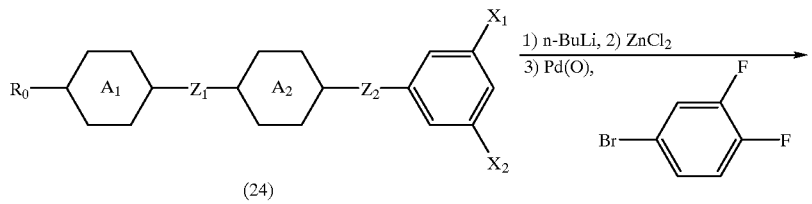

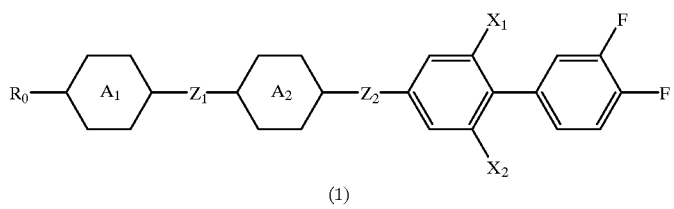

In the formulae showing the above reaction route, $A_1$ and $A_2$ are each independently a trans-1,4-cyclohexylene group, or one group selected from the group consisting of a 1,4-phenylene group, a pyrimidine-2,5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl in which one or more hydrogen atoms on a six-membered ring may be substituted by halogen atoms; $Z_1$ and $Z_2$ are each independently —$(CH_2)_4$—, —$(CH_2)_3O$—, —$O(CH_2)_3$— or a single bond; $X_1$ and $X_2$ are each independently H, F, Cl or Br.

The compound of the present invention in which one or more elements constituting this compound are substituted by isotopes also shows the good characteristics.

EXAMPLES

Next, the present invention will be described in more detail with reference to examples, but the scope of the present invention should not be limited by these examples at all. In the examples, C, N and Iso denote a crystalline phase, a nematic phase and an isotropic liquid phase, respectively. The unit of all phase transition temperatures is ° C. In the case that two crystalline phases are present, they are represented by $C_1$ and $C_2$. Furthermore, the structure of each compound was confirmed by a nuclear magnetic resonance spectrum (hereinafter abbreviated to "$^1$H-NMR"), a mass spectrum (hereinafter abbreviated to "MS") and the like. In the examples, d, t, m and J denote a doublet, a triplet, a multiplet and a coupling constant measured by the NMR, respectively, and M$^+$ means a molecular ion peak measured by the MS.

EXAMPLE 1

Preparation of 1,2-difluoro-4-(2,6-difluoro-4-(trans-4-(4-(trans-4-pentylcyclohexyl)butyl)cyclohexyl)phenyl)benzene [a compound of the general formula (1) in which $R_0$ is a pentyl group, rings $A_1$ and $A_2$ are each a trans-1,4-cyclohexylene group, $Z_1$ is a butylene group, $Z_2$ is a single bond, $X_1$ and $X_2$ are each F (Compound No. 8)]

The compound was prepared by the following 3 steps.

First Step

Under a nitrogen gas stream, 3.13 g (129 mmol) of magnesium was added to 50 ml of THF, and while a reaction temperature was maintained at about 50° C., 300 ml of THF containing 22.7 g (118 mmol) of 3,5-difluoro-1-bromobenzene was added dropwise. After stirring for 1 hour at room temperature, 300 ml of THF containing 30.0 g (97.9 mmol) of 4-(4-(trans-4-pentylcyclohexyl)butyl)cyclohexanone was added dropwise. Next, after stirring at 50 to 60° C. for 2 hours, 200 ml of an aqueous saturated ammonium chloride solution was added, thereby terminating the reaction. The reaction mixture was filtered through Celite, and the solvent was then distilled off under reduced pressure, followed by extraction with 500 ml of toluene. The resulting organic layer was washed 3 times with 200 ml of water, and then dried over anhydrous magnesium sulfate. After drying, 1.50 g of p-toluenesulfonic acid monohydrate was added, and heating was done under reflux for 4 hours. The organic layer was washed 3 times with 200 ml of water, and then dried over anhydrous magnesium sulfate. Next, the solvent was distilled off under reduced pressure, and the resulting residue was purified through silica gel column chromatography (a developing solvent: heptane) to obtain 26.4 g of crude 1,3-difluoro-5-(4-(4-(trans-4-pentylcyclohexyl)butyl)cyclohexene-1-yl)benzene.

Second Step 26.4 g (65.6 mmol) of crude 1,3-difluoro-5-(4-(4-(trans-4-pentylcyclohexyl)butyl)cyclohexene-1-yl)benzene obtained in the above first step was dissolved in 300 ml of a mixed solvent of toluene/ethanol=1/1 (v/v), and 1.32 g of a 5 wt % palladium/carbon catalyst was added, followed by stirring at room temperature for 6 hours under a hydrogen pressure of 1 to 2 kg/cm$^2$. After the catalyst was removed by filtration, the solvent was distilled off under reduced pressure, and the resulting residue was subjected to silica gel column chromatography (a developing solvent: heptane) to obtain 11.3 g of 1,3-difluoro-5-(trans-4-(4-(trans-4-pentylcyclohexyl)butyl)cyclohexyl)benzene.

Third Step

Under a nitrogen gas stream, 6.00 g (14.9 mmol) of 1,3-difluoro-5-(trans-4-(4-(trans-4-pentylcyclohexyl)butyl)cyclohexyl)benzene obtained in the above second step was dissolved in 100 ml of THF, and the solution was then cooled to −30° C. with a refrigeration medium. Next, 11.1 ml of n-butyl lithium (1.6 M, an n-hexane solution) was added dropwise, and the solution was stirred at the same temperature for 20 minutes, cooled to −50° C., and then stirred for 1 hour. 35.7 ml of zinc chloride (0.5 M, a THF solution) was added dropwise, and the solution was stirred at the same temperature for 1 hour, and further stirred at room temperature for 1 hour. Afterward, 0.06 g of tetrakis(triphenylphosphine)palladium (0) was added and 20 ml of a THF solution containing 3.43 g (17.8 mmol) of 3,4-difluorobromobenzene was added dropwise, followed by heating under reflux for 3 hours. The reaction mixture was added to 50 ml of water, and then extracted with 300 ml of toluene. Next, the resulting organic layer was washed 3 times with 100 ml of water, and then dried over anhydrous magnesium sulfate. The solvent was distilled off under reduced pressure, and the resulting residue was purified through silica gel column chromatography (a developing solvent: toluene) to obtain crude 1,2 -difluoro-4-(2,6-difluoro-4-(trans-4-(4-(trans-4-pentylcyclohexyl)butyl) cyclohexyl)phenyl)benzene. This crude product was recrystallized once from heptane, and further recrystallized twice from a mixed solvent of heptane:ethyl acetate=9:1 (v:v), thereby obtaining 4.03 g of the desired compound.

The measured results of this compound by NMR and MS were as follows.

The measured results by $^1$H-NMR: δ (ppm)=0.50–2.80 (m, 39H), 6.80 (d, 2H, $J_{H-F}$=9.2 Hz), 7.10–7.50 (m, 3H)

The measured results by MS: m/e=516 (M$^+$), 265, 252, 239, 97, 55.

The above measured data properly support the structure of the desired compound.

Furthermore, phase transition temperatures of this compound were $C_1$ 76.7 $C_2$ 92.9 N 154.1 Iso, and this compound had a nematic phase.

A measured voltage retention of a display device formed by using this compound was 97.8% at 100° C. On the other hand, a voltage retention at 100° C. of a compound having 3,4,5-trifluorophenyl group represented by the formula (a) mentioned in Japanese Patent Application Laid-open No. 233626/1990 was in the range of 94.2 to 96.0%. Thus, it is apparent that the voltage retention can be improved by the use of the compound of the present invention.

EXAMPLE 2

Preparation of 1,2-difluoro-4-(2,6-difluoro-4-(4-(trans-4-(trans-4-propylcyclohexyl)cyclohexyl)butyl)phenyl) benzene [a compound of the general formula (1) in which $R_0$ is a propyl group, rings $A_1$ and $A_2$ are each a trans-1,4-cyclohexylene group, $Z_1$ is a single bond, $Z_2$ is a butylene group, $X_1$ and $X_2$ are each F (Compound No. 43)]

The compound was prepared by the following 8 steps.

First Step

A mixture of 531 g (1170 mmol) of 2-(1,3-dioxane-2-yl) ethyltriphenylphosphonium bromide and 4.0 l of THF was cooled to −30° C. under a nitrogen gas stream with a refrigeration medium. To this mixture, 121 g (1080 mmol) of t-BuOK was added, followed by stirring for 1 hour. Furthermore, 1 l of a THF solution containing 200 g (899 mmol) of 4-(trans-4-propylcyclohexyl)cyclohexanone was added dropwise to the mixture, while the temperature was maintained at −30° C. or less. After the dropping, the reaction temperature was slowly raised to room temperature, and the solution was further stirred for 5 hours. Next, the reaction solution was filtered through Celite, and the solvent was then distilled off under reduced pressure. The resulting residue was purified through silica gel column chromatography (a developing solvent: a mixed solvent of toluene/ ethyl acetate=9/1 (v/v)) to obtain 277 g of crude 2-(2-(4-(trans-4-propylcyclohexyl)cyclohexylidene)ethyl)-1,3-dioxane.

Second Step 277 g (864 mmol) of crude product obtained in the above first step was dissolved in 3.0 l of a mixed solvent of toluene/ethanol=1/1 (v/v), and 13.9 g of a 5 wt % palladium/ carbon catalyst was added, followed by stirring at room temperature for 6 hours under a hydrogen pressure of 1 to 2 kg/cm$^2$. After the catalyst was removed by filtration, the solvent was distilled off under reduced pressure, and the resulting residue was purified through silica gel column chromatography (a developing solvent: toluene). Recrystallization was carried out from heptane to obtain 167 g of 2-(2-(trans-4-(trans-4-propylcyclohexyl)cyclohexyl)ethyl)-1,3-dioxane.

Third Step 100.0 g (310 mmol) of 2-(2-(trans-4-(trans-4-propylcyclohexyl)cyclohexyl)ethyl)-1,3-dioxane obtained in the above second step was dissolved in 1.0 l of toluene, and 286 g (6210 mmol) of formic acid was added, followed by heating under reflux for 4 hours. Next, the solution was washed twice with 200 ml of an aqueous saturated sodium hydrogencarbonate solution and 5 time with 600 ml of water, and the solvent was then distilled off under reduced pressure to obtain 74.0 g of crude 3 -(trans-4-(trans-4-propylcyclohexyl)cyclohexyl)propanal.

Fourth Step

A mixture of 57.3 g (167 mmol) of methoxymethyl-triphenylphosphonium chloride and 500 ml of THF was cooled to −30° C. under a nitrogen gas stream with a refrigeration medium. 17.3 g (154 mmol) of t-BuOK was added to this mixture, followed by stirring for 1 hour. To this mixture, 300 ml of THF containing 34.0 g (129 mmol) of 3-(trans-4-(trans-4-propylcyclohexyl)cyclohexyl)propanal was added dropwise, while a temperature of −30° C. or less was maintained. After the dropping, a reaction temperature was gradually raised to room temperature, followed by stirring for 5 hours. The reaction mixture was filtered through Celite, and the solvent was then distilled off under reduced pressure. The resulting residue was purified through silica gel column chromatography (a developing solvent: heptane) to obtain 30.3 g of crude 1-methoxy-4-(trans-4-(trans-4-propylcyclohexyl)cyclohexyl)-1-butene.

Fifth Step 30.3 g (104 mmol) of crude 1-methoxy-4-(trans-4-(trans-4-propylcyclohexyl)cyclohexyl)-1-butene obtained by the reaction in the fourth step was dissolved in 300 ml of toluene, and 47.4 g (1030 mmol) of formic acid was added, followed by heating under reflux for 4 hours. Next, the solution was washed twice with 100 ml of an aqueous saturated sodium hydrogencarbonate solution and 5 time with 150 ml of water, and the solvent was then distilled off under reduced pressure to obtain 28.7 g of crude 4-(trans-4-(trans-4-propylcyclohexyl)cyclohexyl)butanal.

Sixth Step

Under a nitrogen gas stream, 3.32 g (136 mmol) of magnesium was added to 50 ml of THF, and 300 ml of a THF solution containing 23.9 g (124 mmol) of 3,5-difluorobromobenzene was added dropwise, while a reaction temperature was maintained at about 50° C. After stirring at room temperature for 1 hour, 300 ml of a solution containing 28.7 g (103 mmol) of 4-(trans-4-(trans-4-propylcyclohexyl) cyclohexyl)butanal obtained by the reaction in the fifth step was added dropwise. After stirring at 50 to 60° C. for 2 hours, 200 ml of an aqueous saturated ammonium chloride solution was added, thereby terminating the reaction. The reaction mixture was filtered through Celite, and the solvent was then distilled off under reduced pressure, followed by extraction with 500 ml of toluene. The resulting organic layer was washed 3 times with 200 ml of water, and then dried over anhydrous magnesium sulfate. After drying, 1.50 g of p-toluenesulfonic acid monohydrate was added, and heating was done under reflux for 4 hours. The organic layer was washed 3 times with 200 ml of water, and then dried over anhydrous magnesium sulfate. Next, the solvent was distilled off under reduced pressure, and the resulting residue was purified through silica gel column chromatography (a developing solvent: heptane) to obtain 18.7 g of crude 1,3-difluoro-5-(4-(trans-4-(trans-4-propylcyclohexyl) cyclohexyl)butenyl)benzene.

Seventh Step 18.7 g (46.4 mmol) of the crudely purified product obtained by the reaction of the sixth step was dissolved in 300 ml of a mixed solvent of toluene/ethanol=1/1 (v/v), and 0.94 g of a 5 wt % palladium/carbon catalyst was added, followed by stirring at room temperature for 6 hours under a hydrogen pressure of 1 to 2 kg/cm$^2$. After the catalyst was removed by filtration, the solvent was distilled off under reduced pressure, and the resulting residue was purified through silica gel column chromatography (a developing solvent: heptane) and then recrystallized from heptane to obtain 12.5 g of 1,3-difluoro-5-(4-(trans-4-(trans-4-propylcyclohexyl)cyclohexyl)butyl)benzene.

Eighth Step

Under a nitrogen gas stream, 6.00 g (15.9 mmol) of 1,3-difluoro-5-(4-(trans-4-(trans-4-propylcyclohexyl)butyl) cyclohexyl)benzene obtained by the reaction in the seventh step was dissolved in 100 ml of THF, and the solution was then cooled to −30° C. with a refrigeration medium. Next, 11.9 ml of n-butyl lithium (1.6 M, an n-hexane solution) was added dropwise, and the solution was stirred at the same temperature for 20 minutes, cooled to −50° C., and then stirred for 1 hour. 38.2 ml of zinc chloride (0.5 M, a THF solution) was added dropwise, and the solution was stirred at the same temperature for 1 hour, and further stirred at room temperature for 1 hour. Afterward, 0.65 g of tetrakis (triphenylphosphine) palladium (0) was added, and 20 ml of a THF solution containing 3.69 g (19.1 mmol) of 3,4-difluorobromobenzene was added dropwise, followed by heating under reflux for 3 hours. The reaction mixture was added to 50 ml of water, and then extracted with 300 ml of toluene. Next, the resulting organic layer was washed 3 times with 100 ml of water, and then dried over anhydrous magnesium sulfate. The solvent was distilled off under reduced pressure, and the resulting residue was purified through silica gel column chromatography (a developing solvent: toluene) to obtain crude 1,2-difluoro-4-(2,6-difluoro-4-(4-(trans-4-(trans-4-propylcyclohexyl) cyclohexyl)butyl)phenyl)benzene. This crudely purified product was recrystallized three times from heptane, thereby obtaining 4.03 g of the desired compound.

The measured results of the thus obtained desired compound by NMR and MS were as follows.

The measured results by $^1$H-NMR: δ (ppm)=0.40– 2.05 (m, 33H), 2.62 (t, 2H, J=7.3 Hz), 6.81 (d, 2H, $J_{H-F}$=9.0 Hz), 7.05–7.52 (m, 3H)

The measured results by MS: m/e=488 (M$^+$), 252, 239, 83, 69.

The above measured data properly support the structure of the desired compound.

Furthermore, phase transition temperatures of this compound were C 94.2 N 157.5 Iso, and this compound had a nematic phase.

EXAMPLE 3

Preparation of 3-(trans-4-(trans-4-propylcyclohexyl) cyclohexyl)propyl 3,5-difluoro-4-(3,4-difluorophenyl) phenyl ether [a compound of the general formula (1) in which R$_0$ is a propyl group, rings A$_1$ and A$_2$ are each a trans-1,4-cyclohexylene group, Z$_1$ is a single bond, Z$_2$ is a propyloxy group, X$_1$ and X$_2$ are each F (Compound No. 115)]

The compound was prepared by the following 4 steps.

First Step

Under a nitrogen gas stream, 200 ml of THF was cooled to 5° C. or less on an ice bath, and 4.31 g (113 mmol) of lithium aluminum hydride was then added, followed by stirring. Next, 200 ml of a THF solution containing 40.0 g (151 mmol) of crude 3-(trans-4-(trans-4-propylcyclohexyl) cyclohexyl)propanal obtained in the third step of Example 2 was added dropwise, while the same temperature was kept, followed by stirring at room temperature for 6 hours. The reaction mixture was slowly added to 50 ml of a 2N aqueous sodium hydroxide solution, and then stirred at 50° C. for 30 minutes. The reaction mixture was filtered through Celite, and the solvent was then distilled off under reduced pressure, followed by extraction with ethyl acetate. Afterward, the extract was dried over anhydrous magnesium sulfate. Next, the solvent was distilled off under reduced pressure to obtain 34.0 g of crude 3-(trans-4-(trans-4-propylcyclohexyl) cyclohexyl)propanol.

Second Step

To 50 ml of xylene, there were added 34.0 g (128 mmol) of crude 3-(trans-4-(trans-4-propylcyclohexyl)cyclohexyl) propanol obtained by the above procedure and 87.9 g (511 mmol) of 47% hydrobromic acid, and water was removed by azeotropic dehydration, followed by stirring at about 150° C. for 2 hours. Afterward, 300 ml of toluene was added, and the solution was washed twice with 200 ml of an aqueous saturated sodium hydrogencarbonate solution and 3 time with 200 ml of water, and then dried over anhydrous magnesium sulfate. Next, the solvent was distilled off under reduced pressure, and the resulting residue was purified through silica gel column chromatography (a developing solvent: heptane) to obtain 16.6 g of crude 1-bromo-3-(trans-4-(trans-4-propylcyclohexyl)cyclohexyl)propane.

Third Step

Under a nitrogen gas stream, 2.98 g (68.2 mmol) of oily 55% sodium hydride was added to 10 ml of N,N-dimethylformamide (DMF), and the mixture was then cooled with water. Next, 50 ml of a DMF solution containing 7.39 g (56.8 mmol) of 3,5-difluorophenol was added dropwise, followed by stirring for 1 hour. 15.6 g (47.4 mmol) of crude 1-bromo-3-(trans-4-(trans-4-propylcyclohexyl) cyclohexyl)propane was dissolved in 40 ml of a mixed solvent of toluene/DMF=⅓ (v/v), and the solution was added dropwise, followed by heating and stirring at about 80° C. for 3 hours. The reaction mixture was added to 50 ml of water, and the resulting organic layer was separated, washed 3 times with 50 ml of water, and then dried over anhydrous magnesium sulfate. Next, the solvent was distilled off under reduced pressure, and the resulting residue was purified through silica gel column chromatography (a developing solvent: heptane) and then recrystallized once from heptane to obtain 8.36 g of 3-(trans-4-(trans-4-propylcyclohexyl)cyclohexyl)propyl 3,5-difluoro ether.

Fourth Step

Under a nitrogen gas stream, 5.00 g (13.2 mmol) of this 3-(trans-4-(trans-4-propylcyclohexyl)cyclohexyl)propyl 3,5-difluoro ether was dissolved in 100 ml of THF, and the mixture was then cooled to −30° C. Next, 9.9 ml of n-butyl lithium (1.6 M, an n-hexane solution) was added dropwise, and the solution was stirred at the same temperature for 20 minutes, cooled to −50° C., and then stirred for 1 hour. 31.7 ml of zinc chloride (0.5 M, a THF solution) was added dropwise, and the solution was stirred at the same temperature for 1 hour, and further stirred at room temperature for 1 hour. Afterward, 0.65 g of tetrakis(triphenylphosphine) palladium (0) was added, and 20 ml of a THF solution containing 3.06 g (15.9 mmol) of 3,4-difluorobromobenzene was added dropwise, followed by heating under reflux for 3 hours. The reaction mixture was added to 50 ml of water, and then extracted with 300 ml of toluene. Next, the resulting organic layer was washed 3 times with 100 ml of water, and then dried over anhydrous magnesium sulfate. The solvent was distilled off under reduced pressure, and the resulting residue was purified through silica gel column chromatography (a developing solvent: toluene) to obtain crude 3-(trans-4-(trans-4-propylcyclohexyl)cyclohexyl)propyl 3,5-difluoro-4-(3,4-difluorophenyl)phenyl ether. This crudely purified product was recrystallized three times from heptane, thereby obtaining 1.76 g of the desired compound.

The measured results of the thus obtained desired compound by NMR and MS were as follows.

The measured results by $^1$H-NMR: δ (ppm)=0.52–2.10 (m, 31H), 3.93 (t, 2H, J=6.5 Hz), 6.52 (d, 2H, $J_{H-F}$=9.9 Hz), 7.10–7.50 (m, 3H)

The measured results by MS: m/e=490 (M$^+$), 242, 123, 83, 69.

The above measured data properly support the structure of the desired compound.

Furthermore, phase transition temperatures of this compound were C 94.2 N 157.5 Iso, and this compound had a nematic phase.

The following compounds can be prepared in accordance with the procedures of Examples 1 to 3.

| Compound No. | R$_0$ | A$_1$—Z$_1$—A$_2$—Z$_2$ | X$_1$ | X$_2$ | |
|---|---|---|---|---|---|
| 1 | C$_3$H$_7$ | 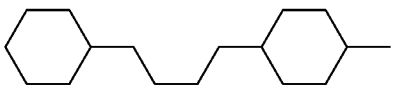 | H | H | |
| 2 | C$_5$H$_{11}$ | 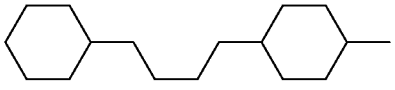 | H | H | |
| 3 | C$_7$H$_{15}$ | 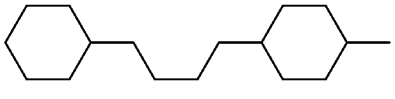 | H | H | |
| 4 | C$_3$H$_7$ | 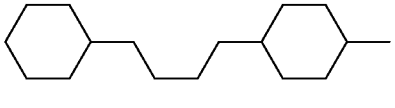 | F | H | |
| 5 | C$_5$H$_{11}$O | 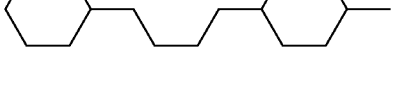 | F | H | |
| 6 | C$_7$H$_{15}$ | 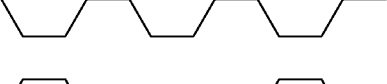 | F | H | |
| 7 | C$_3$H$_7$ | 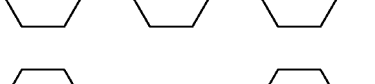 | F | F | |
| 8 | C$_5$H$_{11}$ | 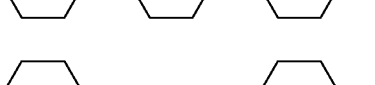 | F | F | C1 76.7 C2 92.9 N 154.1 Iso |
| 9 | C$_7$H$_{15}$ | 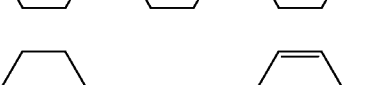 | F | F | |
| 10 | C$_3$H$_7$ | 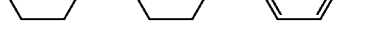 | H | H | |

-continued
| Compound No. | R₀ | A₁—Z₁—A₂—Z₂ | X₁ | X₂ |
|---|---|---|---|---|
| 11 | C₅H₁₁ | 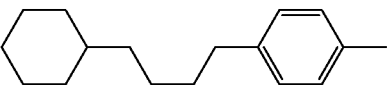 | H | H |
| 12 | C₇H₁₅ | 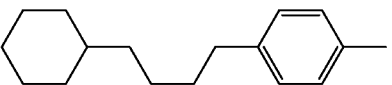 | H | H |
| 13 | C₃H₇ |  | F | H |
| 14 | C₅H₁₁ | 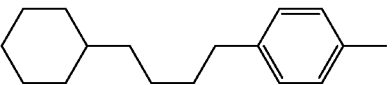 | F | H |
| 15 | 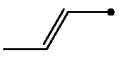 | 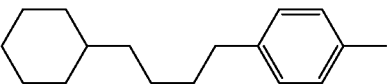 | F | H |
| 16 | C₃H₇ | 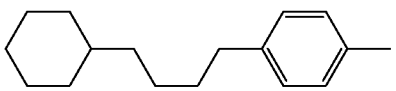 | F | F |
| 17 | C₅H₁₁ | 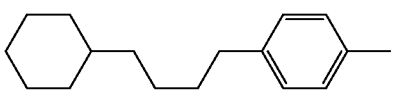 | F | F |
| 18 | C₃H₇O | 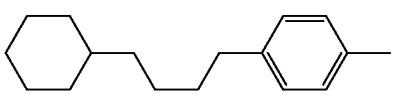 | F | F |
| 19 | C₃H₇ | 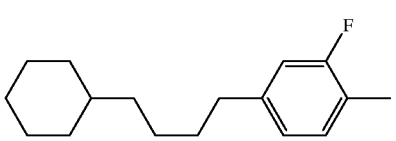 | H | H |
| 20 | C₅H₁₁ | 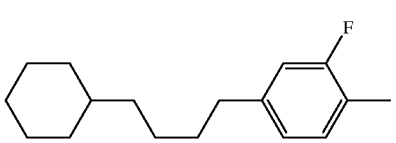 | H | H |
| 21 | C₇H₁₅ | 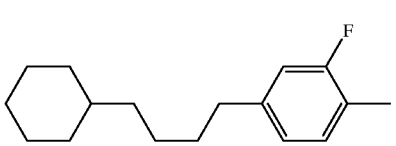 | H | H |
| 22 | C₃H₇ | 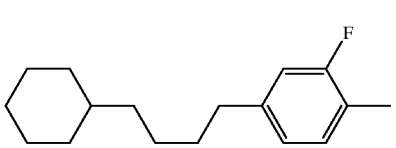 | F | H |

-continued
| Compound No. | $R_0$ | $A_1-Z_1-A_2-Z_2$ | $X_1$ | $X_2$ |
|---|---|---|---|---|
| 23 | 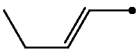 |  | F | H |
| 24 | $C_7H_{15}$ |  | F | H |
| 25 | $C_3H_7$ |  | F | F |
| 26 | $C_5H_{11}$ |  | F | F |
| 27 | $C_7H_{15}O$ |  | F | F |
| 28 | $C_3H_7$ |  | H | H |
| 29 | $C_5H_{11}$ |  | H | H |
| 30 |  | | H | H |
| 31 | $C_3H_7$ | | F | H |

-continued

| Compound No. | R₀ | A₁—Z₁—A₂—Z₂ | X₁ | X₂ |
|---|---|---|---|---|
| 32 | C₅H₁₁O | Cyclohexyl-(CH₂)₃-(3,4,5-trifluorophenyl)- | F | H |
| 33 | C₇H₁₅ | Cyclohexyl-(CH₂)₃-(3,4,5-trifluorophenyl)- | F | H |
| 34 | C₃H₇ | Cyclohexyl-(CH₂)₃-(3,4,5-trifluorophenyl)- | F | F |
| 35 | CH₂=CHCH₂CH₂– | Cyclohexyl-(CH₂)₃-(3,4,5-trifluorophenyl)- | F | F |
| 36 | C₇H₁₅ | Cyclohexyl-(CH₂)₃-(3,4,5-trifluorophenyl)- | F | F |
| 37 | C₃H₇ | Cyclohexyl-cyclohexyl-(CH₂)₃– | H | H |
| 38 | C₅H₁₁O | Cyclohexyl-cyclohexyl-(CH₂)₃– | H | H |
| 39 | C₇H₁₅ | Cyclohexyl-cyclohexyl-(CH₂)₃– | H | H |
| 40 | C₃H₇ | Cyclohexyl-cyclohexyl-(CH₂)₃– | F | H |
| 41 | C₅H₁₁ | Cyclohexyl-cyclohexyl-(CH₂)₃– | F | H |

-continued
| Compound No. | R₀ | A₁—Z₁—A₂—Z₂ | X₁ | X₂ | |
|---|---|---|---|---|---|
| 42 | C₇H₁₅ | 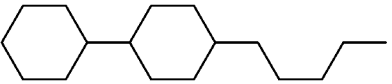 | F | H | |
| 43 | C₃H₇ | 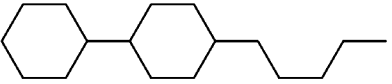 | F | F | C 94.2 N 157.5 Iso |
| 44 | C₅H₁₁ | 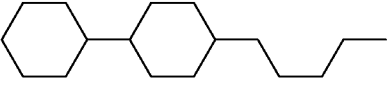 | F | F | |
| 45 | C₇H₁₅ | 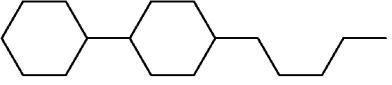 | F | F | |
| 46 | C₃H₇ | 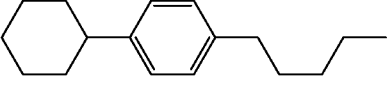 | H | H | |
| 47 | C₅H₁₁ | 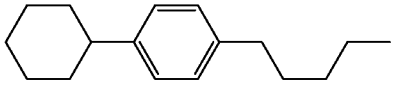 | H | H | |
| 48 | 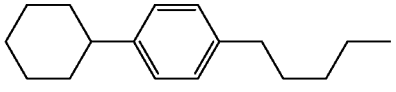 | 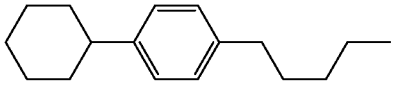 | H | H | |
| 49 | C₃H₇ | 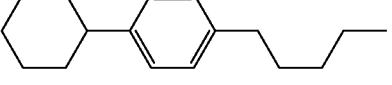 | F | H | |
| 50 | C₅H₁₁ | 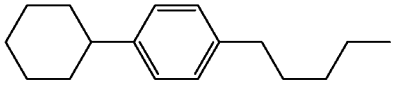 | F | H | |
| 51 | C₇H₁₅O | 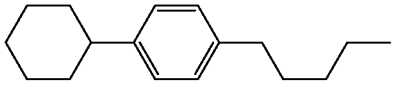 | F | H | |
| 52 | C₃H₇ | 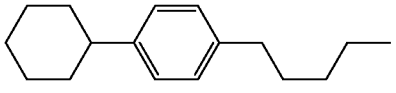 | F | F | |
| 53 | C₅H₁₁ | 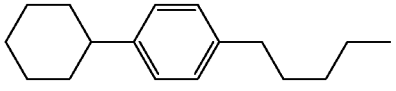 | F | F | |
| 54 | C₇H₁₅ | 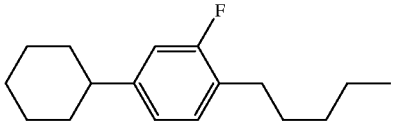 | F | F | |
| 55 | C₃H₇ |  | H | H | |

-continued
| Compound No. | R₀ | A₁—Z₁—A₂—Z₂ | X₁ | X₂ |
|---|---|---|---|---|
| 56 | C₅H₁₁ | 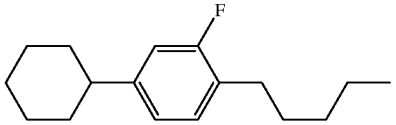 | H | H |
| 57 | C₇H₁₅ | 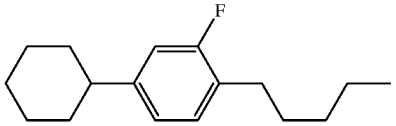 | H | H |
| 58 | 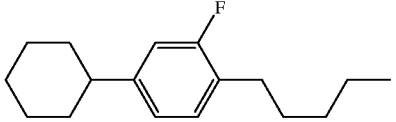 | 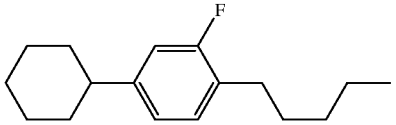 | F | H |
| 59 | C₅H₁₁ | 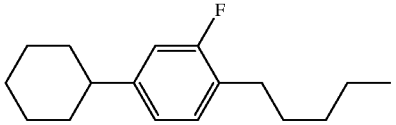 | F | H |
| 60 | C₇H₁₅ | 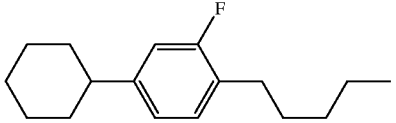 | F | H |
| 61 | C₃H₇O | 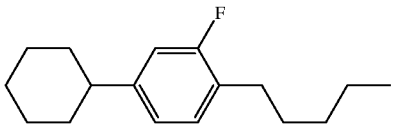 | F | F |
| 62 | C₅H₁₁ | 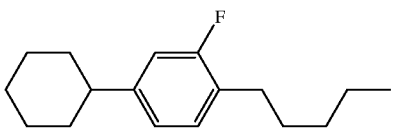 | F | F |
| 63 | 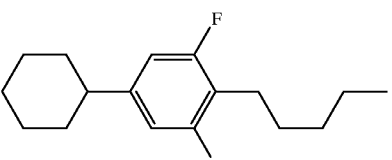 | | F | F |
| 64 | C₃H₇ | | H | H |

-continued
| Compound No. | R₀ | A₁—Z₁—A₂—Z₂ | X₁ | X₂ |
|---|---|---|---|---|
| 65 | $C_5H_{11}O$ | 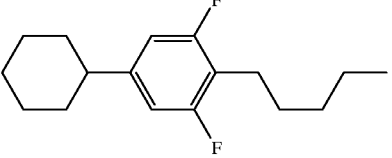 | H | H |
| 66 | $C_7H_{15}$ | 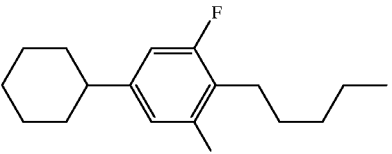 | H | H |
| 67 | $C_3H_7$ | 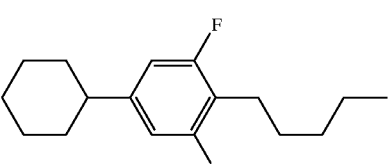 | F | H |
| 68 | $C_5H_{11}$ | 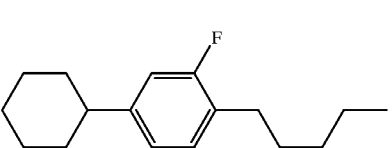 | F | H |
| 69 | $C_7H_{15}$ | 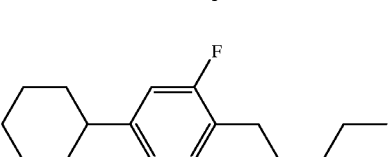 | F | H |
| 70 | $C_3H_7$ | 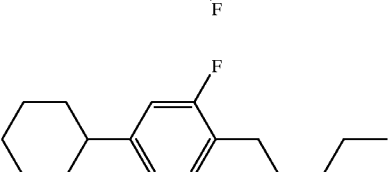 | F | F |
| 71 | 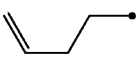 | 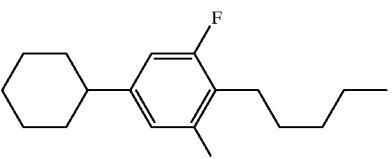 | F | F |
| 72 | $C_7H_{15}$ | 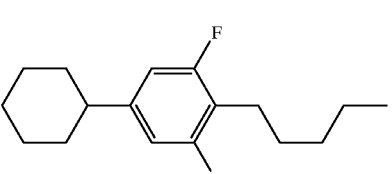 | F | F |

-continued
| Compound No. | R₀ | A₁—Z₁—A₂—Z₂ | X₁ | X₂ |
|---|---|---|---|---|
| 73 | C₃H₇ | 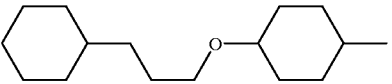 | H | H |
| 74 | C₅H₁₁ | 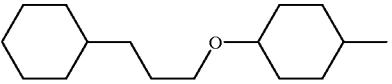 | H | H |
| 75 | C₇H₁₅ | 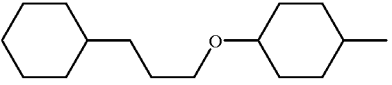 | H | H |
| 76 | C₃H₇O | 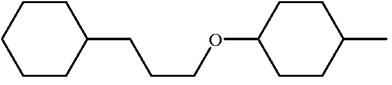 | F | H |
| 77 | C₅H₁₁ | 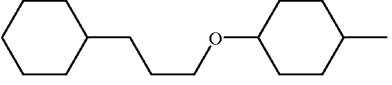 | F | H |
| 78 | C₇H₁₅ | 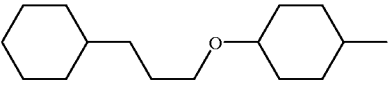 | F | H |
| 79 | C₃H₇ | 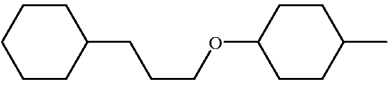 | F | F |
| 80 | C₅H₁₁ | 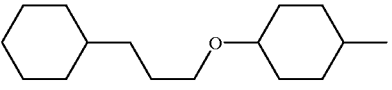 | F | F |
| 81 | 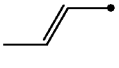 | 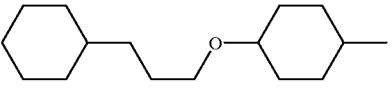 | F | F |
| 82 | C₃H₇ | 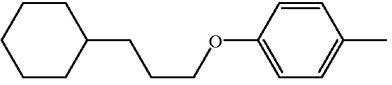 | H | H |
| 83 | C₅H₁₁ | 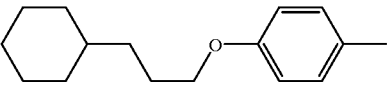 | H | H |
| 84 | C₇H₁₅ | 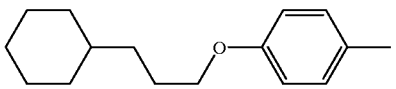 | H | H |
| 85 | C₃H₇ | 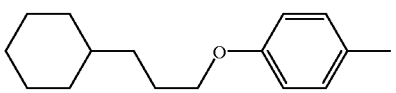 | F | H |
| 86 | C₅H₁₁ | 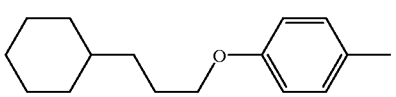 | F | H |

-continued
| Compound No. | R₀ | A₁—Z₁—A₂—Z₂ | X₁ | X₂ |
|---|---|---|---|---|
| 87 | $C_7H_{15}$ | 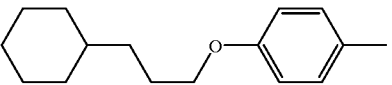 | F | H |
| 88 | $C_3H_7$ | 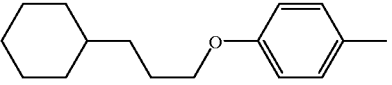 | F | F |
| 89 | $C_5H_{11}O$ | 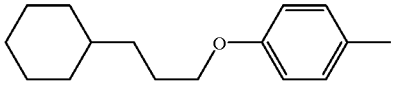 | F | F |
| 90 | $C_7H_{15}$ | 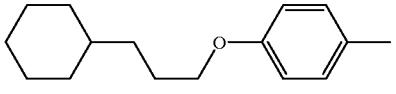 | F | F |
| 91 | $C_3H_7$ | 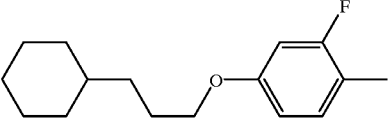 | H | H |
| 92 | $C_5H_{11}$ | 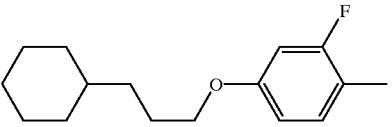 | H | H |
| 93 | $C_7H_{15}O$ | 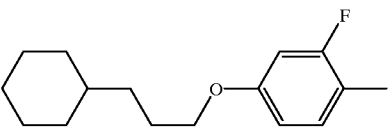 | H | H |
| 94 |  | 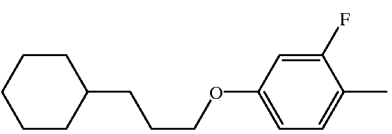 | F | H |
| 95 | $C_5H_{11}$ | 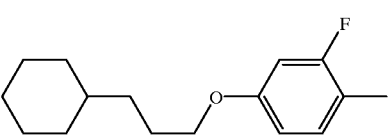 | F | H |
| 96 | $C_7H_{15}$ | 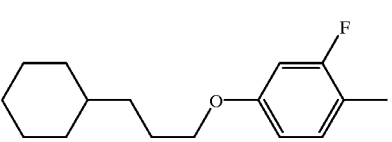 | F | H |
| 97 | $C_3H_7$ | 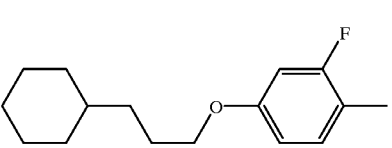 | F | F |

-continued
| Compound No. | R₀ | A₁—Z₁—A₂—Z₂ | X₁ | X₂ |
|---|---|---|---|---|
| 98 | $C_5H_{11}$ | 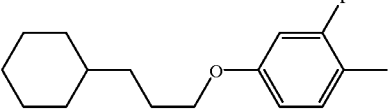 | F | F |
| 99 | $C_7H_{15}$ | 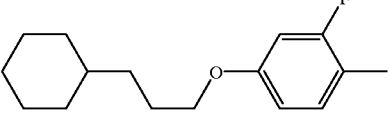 | F | F |
| 100 | $C_3H_7$ | 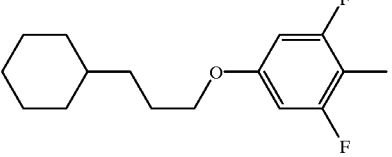 | H | H |
| 101 |  | 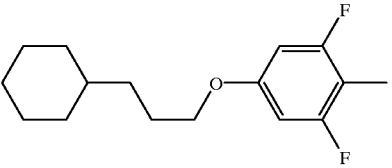 | H | H |
| 102 | $C_7H_{15}$ | 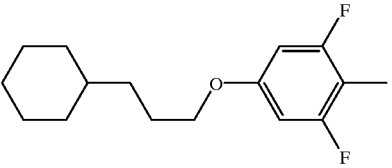 | H | H |
| 103 | $C_3H_7$ | 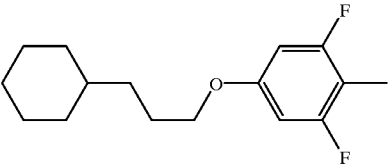 | F | H |
| 104 | $C_5H_{11}$ | 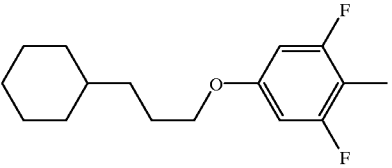 | F | H |
| 105 | $C_7H_{15}$ | 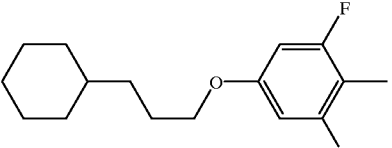 | F | H |

-continued

| Compound No. | R₀ | A₁—Z₁—A₂—Z₂ | X₁ | X₂ |    |
|---|---|---|---|---|---|
| 106 | $C_3H_7O$ | | F | F | |
| 107 | $C_5H_{11}$ | | F | F | |
| 108 | $C_7H_{15}$ | | F | F | |
| 109 | $C_3H_7$ | | H | H | |
| 110 | $C_5H_{11}$ | | H | H | |
| 111 | $C_7H_{15}O$ | | H | H | |
| 112 | $C_3H_7$ | | F | H | |
| 113 | $C_5H_{11}$ | | F | H | |
| 114 | $C_7H_{15}$ | | F | H | |
| 115 | $C_3H_7$ | | F | F | C 70.0 N 165.0 Iso |
| 116 | $C_5H_{11}$ | | F | F | |
| 117 | $C_7H_{15}$ | | F | F | |

-continued
| Compound No. | R₀ | A₁—Z₁—A₂—Z₂ | X₁ | X₂ |
|---|---|---|---|---|
| 118 | C₃H₇ | 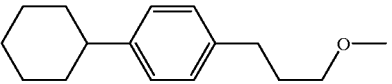 | H | H |
| 119 | C₅H₁₁O | 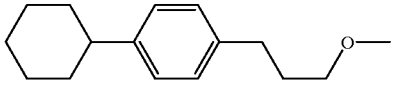 | H | H |
| 120 | C₇H₁₅ | 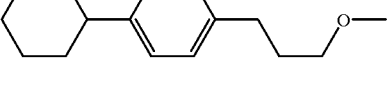 | H | H |
| 121 | C₃H₇ | 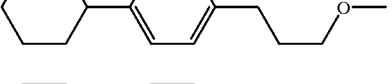 | F | H |
| 122 | C₅H₁₁ | 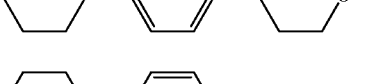 | F | H |
| 123 | C₇H₁₅ | 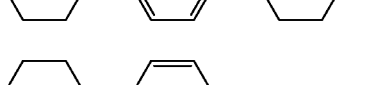 | F | H |
| 124 | C₃H₇ |  | F | F |
| 125 | 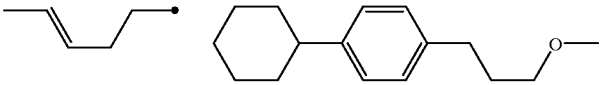 | 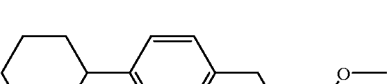 | F | F |
| 126 | C₇H₁₅ | 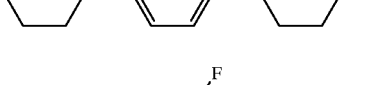 | F | F |
| 127 | C₃H₇ | 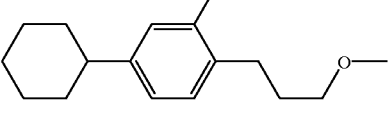 | H | H |
| 128 | C₅H₁₁ | 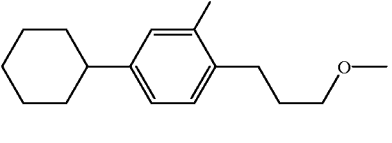 | H | H |
| 129 | C₇H₁₅ | 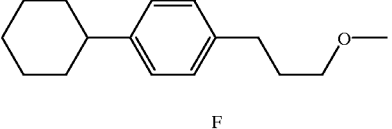 | H | H |
| 130 | 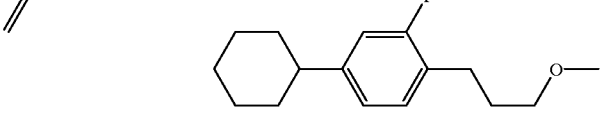 | 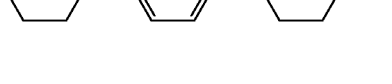 | F | H |

-continued
| Compound No. | R₀ | A₁—Z₁—A₂—Z₂ | X₁ | X₂ |
|---|---|---|---|---|
| 131 | C₅H₁₁ | 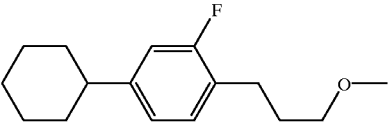 | F | H |
| 132 | C₇H₁₅ | 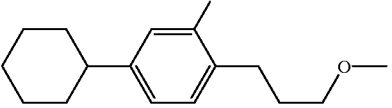 | F | H |
| 133 | C₃H₇O | 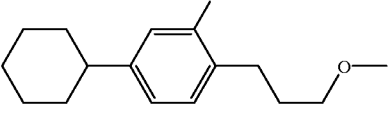 | F | F |
| 134 | C₅H₁₁ | 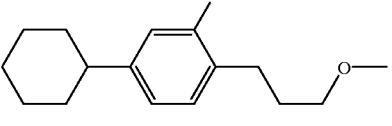 | F | F |
| 135 | C₇H₁₅ | 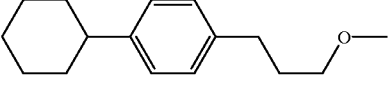 | F | F |
| 136 | C₃H₇ | 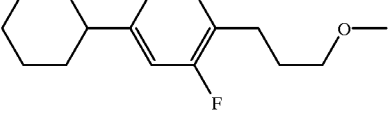 | H | H |
| 137 | C₅H₁₁O | 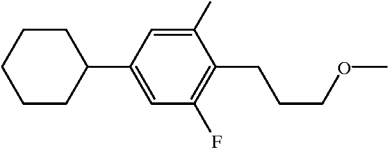 | H | H |
| 138 | C₇H₁₅ | 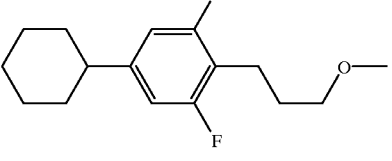 | H | H |
| 139 | C₃H₇ | 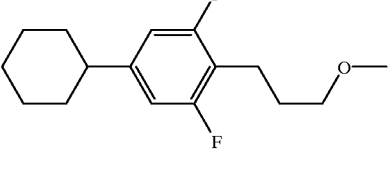 | F | H |

-continued

| Compound No. | $R_0$ | $A_1-Z_1-A_2-Z_2$ | $X_1$ | $X_2$ |
|---|---|---|---|---|
| 140 | $C_5H_{11}$ | cyclohexyl-(2,6-difluorophenyl)-CH2CH2CH2-O-CH3 | F | H |
| 141 | CH3-CH=CH-CH2• | cyclohexyl-(2,6-difluorophenyl)-CH2CH2CH2-O-CH3 | F | H |
| 142 | $C_3H_7$ | cyclohexyl-(2,6-difluorophenyl)-CH2CH2CH2-O-CH3 | F | F |
| 143 | $C_5H_{11}$ | cyclohexyl-(2,6-difluorophenyl)-CH2CH2CH2-O-CH3 | F | F |
| 144 | $C_7H_{15}$ | cyclohexyl-(2,6-difluorophenyl)-CH2CH2CH2-O-CH3 | F | F |
| 145 | $C_3H_7$ | cyclohexyl-O-CH2CH2-cyclohexyl | H | H |
| 146 | $C_5H_{11}$ | cyclohexyl-O-CH2CH2-cyclohexyl | H | H |
| 147 | $C_7H_{15}$ | cyclohexyl-O-CH2CH2-cyclohexyl | H | H |
| 148 | $C_3H_7$ | cyclohexyl-O-CH2CH2-cyclohexyl | F | H |
| 149 | $C_5H_{11}$ | cyclohexyl-O-CH2CH2-cyclohexyl | F | H |

-continued
| Compound No. | R₀ | A₁—Z₁—A₂—Z₂ | X₁ | X₂ |
|---|---|---|---|---|
| 150 | C₃H₇O | 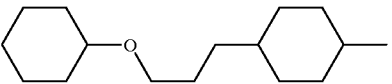 | F | H |
| 151 | C₃H₇ | 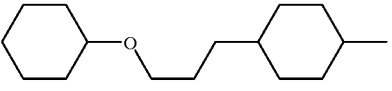 | F | F |
| 152 | C₅H₁₁ |  | F | F |
| 153 |  |  | F | F |
| 154 | C₃H₇ |  | H | H |
| 155 | C₅H₁₁ | 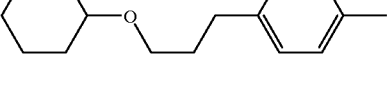 | H | H |
| 156 | C₇H₁₅ | 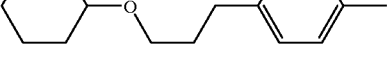 | H | H |
| 157 | C₃H₇ | 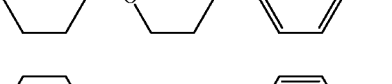 | F | H |
| 158 | C₅H₁₁ | 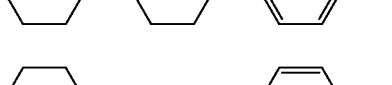 | F | H |
| 159 | C₅H₁₁O | 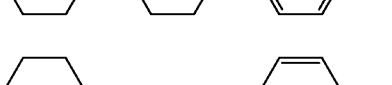 | F | H |
| 160 | C₃H₇ |  | F | F |
| 161 | C₅H₁₁ | 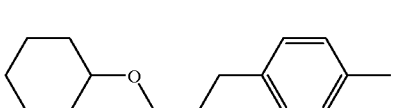 | F | F |
| 162 | C₇H₁₅ | 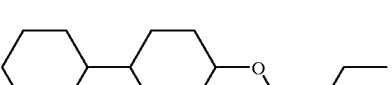 | F | F |
| 163 | C₃H₇ | 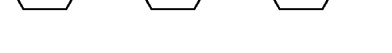 | H | H |

-continued

| Compound No. | R₀ | A₁—Z₁—A₂—Z₂ | X₁ | X₂ |
|---|---|---|---|---|
| 164 | C₅H₁₁ | | H | H |
| 165 | C₇H₁₅ | | H | H |
| 166 | C₃H₇ | | F | H |
| 167 | C₅H₁₁ | | F | H |
| 168 | C₇H₁₅O | | F | H |
| 169 | C₃H₇ | | F | F |
| 170 | C₅H₁₁ | | F | F |
| 171 | C₇H₁₅ | | F | F |
| 172 | C₃H₇ | | H | H |
| 173 | C₅H₁₁ | | H | H |
| 174 | C₅H₁₁O | | H | H |
| 175 | C₃H₇ | | F | H |
| 176 | C₅H₁₁ | | F | H |
| 177 | C₇H₁₅ | | F | H |

-continued
| Compound No. | R₀ | A₁—Z₁—A₂—Z₂ | X₁ | X₂ |
|---|---|---|---|---|
| 178 | C₃H₇ | 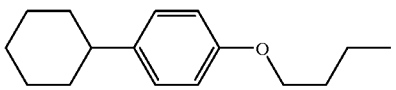 | F | F |
| 179 | C₅H₁₁ | 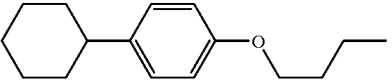 | F | F |
| 180 | 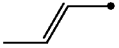 | 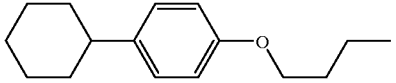 | F | F |
| 181 | C₃H₇ | 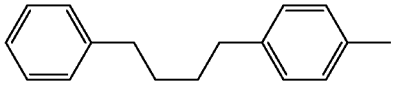 | H | H |
| 182 | C₅H₁₁ | 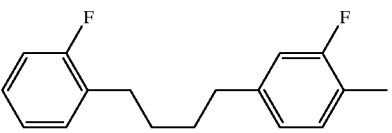 | H | F |
| 183 | C₃H₇ | 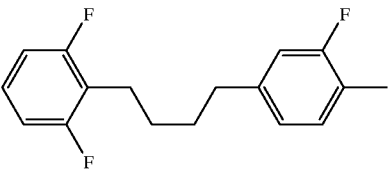 | F | F |
| 184 | C₅H₁₁ | 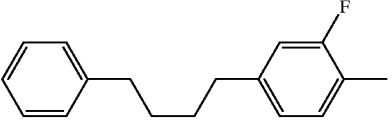 | H | H |
| 185 | C₃H₇ | 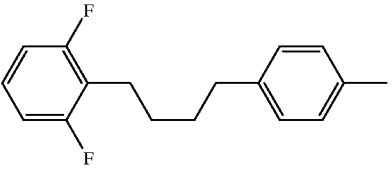 | H | F |
| 186 | C₅H₁₁ | 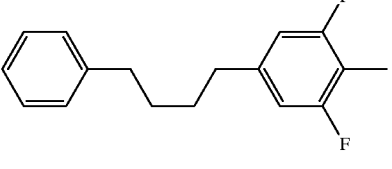 | F | F |
| 187 | C₃H₇ | 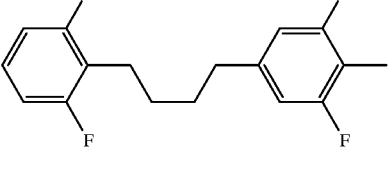 | H | H |

-continued
| Compound No. | R₀ | A₁—Z₁—A₂—Z₂ | X₁ | X₂ |
|---|---|---|---|---|
| 188 | $C_5H_{11}O$ | 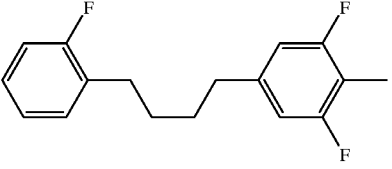 | H | F |
| 189 | $C_3H_7$ | 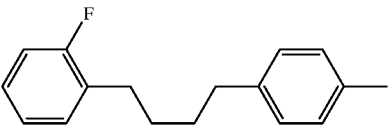 | F | F |
| 190 | $C_5H_{11}$ | 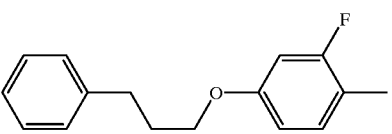 | H | H |
| 191 | $C_3H_7$ | 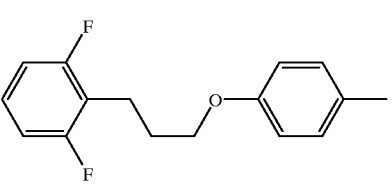 | H | F |
| 192 | $C_5H_{11}$ | 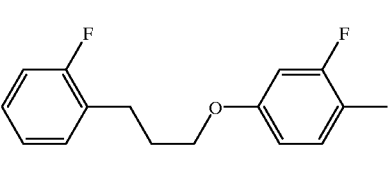 | F | F |
| 193 | $C_3H_7O$ | 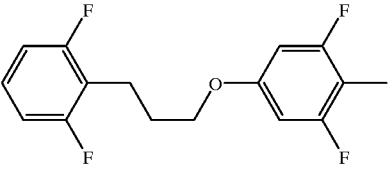 | H | H |
| 194 | $C_5H_{11}$ | 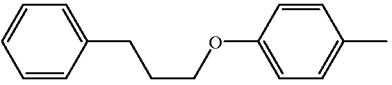 | H | F |
| 195 | $C_3H_7$ | 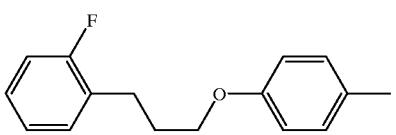 | F | F |
| 196 | $C_5H_{11}$ | 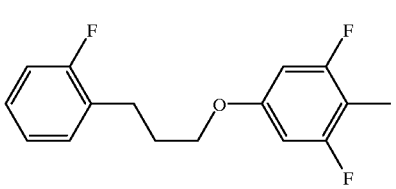 | H | H |

-continued

| Compound No. | $R_0$ | $A_1-Z_1-A_2-Z_2$ | $X_1$ | $X_2$ |
|---|---|---|---|---|
| 197 | $C_3H_7$ | | H | F |
| 198 | $C_5H_{11}$ | | F | F |
| 199 | $C_3H_7$ | | H | H |
| 200 | $C_5H_{11}$ | | H | F |
| 201 | $C_3H_7$ | | F | F |
| 202 | $C_5H_{11}$ | | H | H |
| 203 | | | H | F |
| 204 | $C_5H_{11}$ | | F | F |
| 205 | $C_3H_7$ | | H | H |

| Compound No. | R₀ | A₁—Z₁—A₂—Z₂ | X₁ | X₂ |
|---|---|---|---|---|
| 206 | C₅H₁₁O | 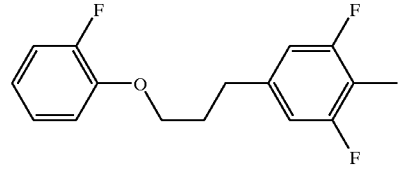 | H | F |
| 207 | C₃H₇ | 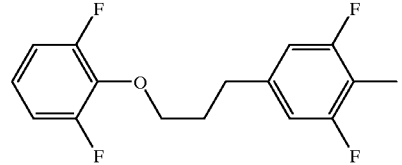 | F | F |
| 208 | C₃H₇ | 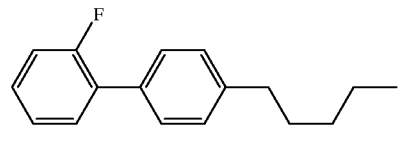 | H | H |
| 209 | C₅H₁₁ | 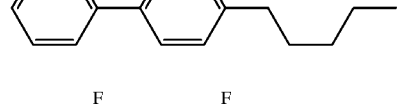 | H | F |
| 210 | C₃H₇ | 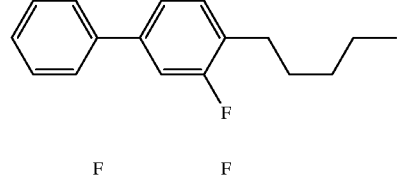 | F | F |
| 211 | C₅H₁₁ | 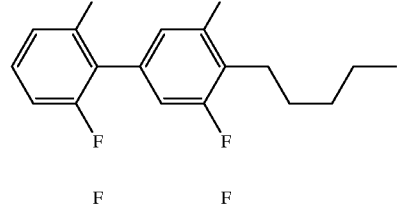 | H | H |
| 212 | C₃H₇ | 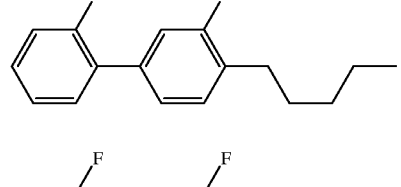 | H | F |
| 213 | 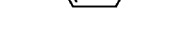 | 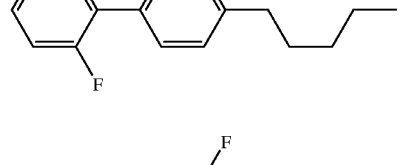 | F | F |
| 214 | C₃H₇ | 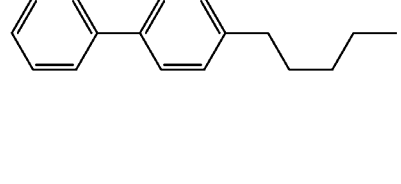 | H | H |

| Compound No. | R₀ | A₁—Z₁—A₂—Z₂ | X₁ | X₂ |
|---|---|---|---|---|
| 215 | C₅H₁₁ | 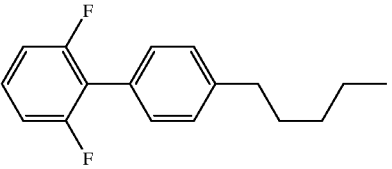 | H | F |
| 216 | C₃H₇ | 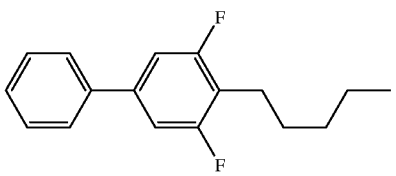 | F | F |
| 217 | C₅H₁₁ | 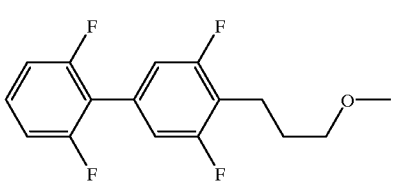 | H | H |
| 218 | C₃H₇O | 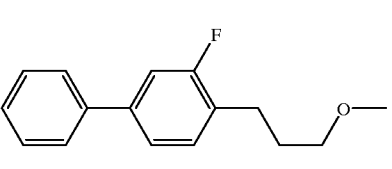 | H | F |
| 219 | C₅H₁₁ | 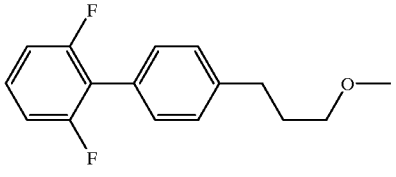 | F | F |
| 220 | C₃H₇ | 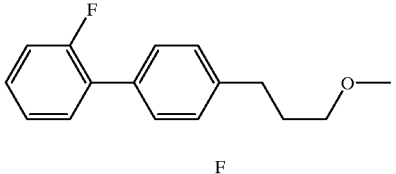 | H | H |
| 221 | C₅H₁₁ | 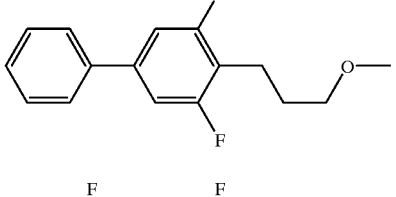 | H | F |
| 222 | C₃H₇ | 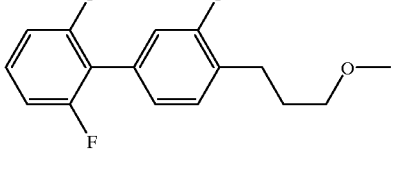 | F | F |
| 223 | C₃H₇ | 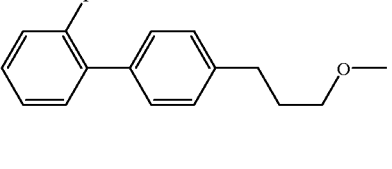 | H | H |

-continued

| Compound No. | R₀ | A₁—Z₁—A₂—Z₂ | X₁ | X₂ |
|---|---|---|---|---|
| 224 | C₅H₁₁ | | H | F |
| 225 | C₃H₇ | | F | F |
| 226 | C₅H₁₁ | | H | H |
| 227 | C₃H₇ | | H | F |
| 228 | C₅H₁₁ | | F | F |
| 229 | C₃H₇ | | H | H |
| 230 | C₅H₁₁ | | H | F |
| 231 | C₃H₇ | | F | F |
| 232 | C₅H₁₁ | | H | H |

-continued

| Compound No. | R₀ | A₁—Z₁—A₂—Z₂ | X₁ | X₂ |
|---|---|---|---|---|
| 233 | C₃H₇ | 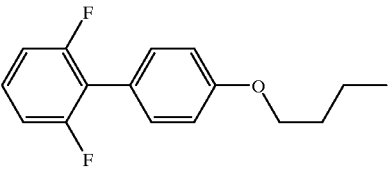 | H | F |
| 234 | C₅H₁₁O | 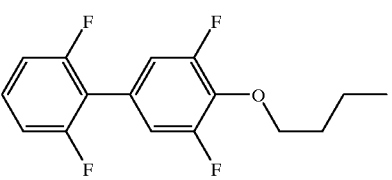 | F | F |

Furthermore, examples of nematic liquid crystal compositions containing the compounds of the present invention are as follows (Use Examples 1 to 26). However, the compounds in the exemplary compositions are represented by abbreviations in accordance with the following rule. That is to say, left terminal groups were represented by n, nO, nOm, V, Vn, nVm and nVmVk; bond groups were represented by 2, 4, E, T, V, CF₂O, OCF₂ and 3O; ring structures were represented by B, B(F), B(F,F), H, Py, D and Ch; and right terminal groups were represented by F, CL, C, CF₃, OCF₃, OCF₂H, n, On, EMe, nV, mVn, mVnF and VFF.

TABLE 1

Representation of Compounds by Use of Symbols
R—(A₁)—Z₁— ... —Zₙ—(Aₙ)—X

1) Left Terminal

| Group R— | Symbol |
|---|---|
| $C_nH_{2n+1}$— | n- |
| $C_nH_{2n+1}O$— | nO— |
| $C_nH_{2n+1}OC_mH_{2m}$— | nOm- |
| $CH_2$=CH— | V— |
| $CH_2$=CHC_nH_{2n}— | Vn- |
| $C_nH_{2n+1}CH$=CHC_mH_{2m}— | nVm- |
| $C_nH_{2n+1}CH$=CHC_mH_{2m}CH=CHC_kH_{2k}— | n-VmVk- |

2) Ring Structure

| —(A₁)—, —(Aₙ)— | Symbol |
|---|---|
| 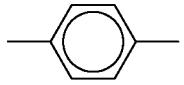 | B |
| 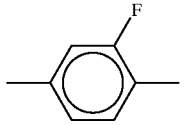 | B(F) |

TABLE 1-continued

Representation of Compounds by Use of Symbols
R—(A₁)—Z₁— ... —Zₙ—(Aₙ)—X

| | Symbol |
|---|---|
| (tetrafluorophenyl) | B(F,F) |
| (cyclohexyl) | H |
| (pyrimidine) | Py |
| (dioxane) | D |
| (cyclohexene) | Ch |

3) Bond Group

| —Z₁—, —Zₙ— | Symbol |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF2 |
| —C₃H₆O— | 3O |

TABLE 1-continued

Representation of Compounds by Use of Symbols
R—(A$_1$)—Z$_1$— . . . —Z$_n$—(A$_n$)—X

4) Right Terminal

| Group —X | Symbol |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —C$_n$H$_{2n+1}$ | -n |
| —OC$_n$H$_{2n+1}$ | —On |
| —COOCH$_3$ | —EMe |
| —C$_n$H$_{2n}$CH=CH$_2$ | -nV |
| —C$_m$H$_{2m}$CH=CHC$_n$H$_{2n+1}$ | -mVn |
| —C$_m$H$_{2m}$CH=CHC$_n$H$_{2n}$F | -mVnF |
| —CH=CF$_2$ | —VFF |

5) Examples of Representation

Ex. 1 3-H2B(F,F)B(F)—F

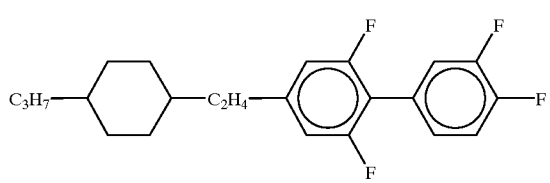

Ex. 2 3-HB(F)TB-2

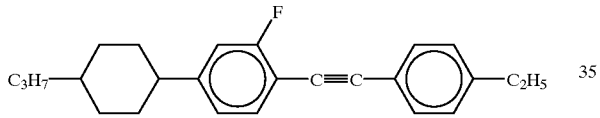

Ex. 3 1V2-BEB(F,F)—C

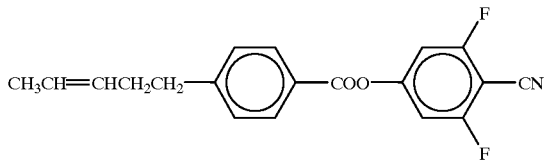

(in this table, n, m and k are each an integer).

The measurement temperature of a viscosity ($\eta$) was 20.0° C.; and the measurement temperatures of a refractive index anisotropy ($\Delta n$), a dielectric anisotropy ($\Delta \epsilon$) and a threshold voltage ($V_{th}$) were 25.0° C., respectively. In addition, % is based on weight.

Example 4 (Use Example 1)

| | |
|---|---|
| 5-H4HB (F, F) B (F)-F | 4.0% |
| 3-HH4B (F, F) B (F)-F | 5.0% |
| 1V2-BEB (F, F)-C | 5.0% |
| 3-HB-C | 26.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-HB (F) TB-3 | 6.0% |

$T_{NI}$ = 88.7 (° C.)
$\eta$ = 19.0 (mPa · s)
$\Delta n$ = 0.152
$\Delta \epsilon$ = 7.6
$V_{th}$ = 1.90 (V)

Example 5 (Use Example 2)

| | |
|---|---|
| 3-HH4B (F, F) B (F)-F | 5.0% |
| 3-HH3OB (F, F) B (F)-F | 5.0% |
| V2-HB-C | 12.0% |
| 1V2-HB-C | 12.0% |
| 3-HB-C | 24.0% |
| 3-HB (F)-C | 5.0% |
| 2-BTB-1 | 2.0% |
| 3-HH-4 | 8.0% |
| 3-HH-VFF | 6.0% |
| 2-HHB-C | 3.0% |
| 3-HHB-C | 6.0% |
| 3-HB (F) TB-2 | 8.0% |
| 3-H2BTB-4 | 4.0% |

$T_{NI}$ = 90.1 (° C.)
$\eta$ = 23.8 (mPa · s)
$\Delta n$ = 0.144
$\Delta \epsilon$ = 9.4
$V_{th}$ = 1.79 (V)

Example 6 (Use Example 3)

| | |
|---|---|
| 5-H4HB (F, F) B (F)-F | 4.0% |
| 3-HH3OB (F, F) B (F)-F | 5.0% |
| 2O1-BEB (F)-C | 5.0% |
| 3O1-BEB (F)-C | 15.0% |
| 4O1-BEB (F)-C | 13.0% |
| 5O1-BEB (F)-C | 12.0% |
| 2-HHB (F)-C | 15.0% |
| 3-HHB (F)-C | 15.0% |
| 3-HB (F) TB-3 | 4.0% |
| 3-HB (F) TB-4 | 4.0% |
| 3-HHB-1 | 4.0% |
| 3-HHB-O1 | 4.0% |

$T_{NI}$ = 92.9 (° C.)
$\eta$ = 91.7 (mPa · s)
$\Delta n$ = 0.147
$\Delta \epsilon$ = 31.4
$V_{th}$ = 0.85 (V)

Example 7 (Use Example 4)

| | |
|---|---|
| 5-H4HB (F, F) B (F)-F | 3.0% |
| 3-HH4B (F, F) B (F)-F | 3.0% |
| 3-HH3OB (F, F) B (F)-F | 3.0% |
| 5-PyB-F | 4.0% |
| 3-PyB (F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 2.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-4 | 5.0% |

$T_{NI}$ = 94.0 (° C.)
$\eta$ = 39.6 (mPa · s)
$\Delta n$ = 0.193
$\Delta \epsilon$ = 6.5
$V_{th}$ = 2.24 (V)

-continued

Example 8 (Use Example 5)

| | |
|---|---|
| 5-H4HB (F, F) B (F)-F | 4.0% |
| 3-DB-C | 10.0% |
| 4-DB-C | 10.0% |
| 2-BEB-C | 12.0% |
| 3-BEB-C | 4.0% |
| 3-PyB (F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 2.0% |
| 3-HHEBB-C | 3.0% |
| 3-HBEBB-C | 3.0% |
| 5-HBEBB-C | 3.0% |

$T_{NI} = 69.0$ (° C.)
$\eta = 41.7$ (mPa · s)
$\Delta n = 0.121$
$\Delta \epsilon = 11.7$
$V_{th} = 1.28$ (V)

Example 9 (Use Example 6)

| | |
|---|---|
| 3-HH4B (F, F) B (F)-F | 5.0% |
| 3-HB-C | 18.0% |
| 5-HB-C | 3.0% |
| 1O1-HB-C | 10.0% |
| 3-HB (F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 3.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

$T_{NI} = 80.2$ (° C.)
$\eta = 20.5$ (mPa · s)
$\Delta n = 0.140$
$\Delta \epsilon = 8.4$
$V_{th} = 1.72$ (V)

Example 10 (Use Example 7)

| | |
|---|---|
| 3-HH3OB (F, F) B (F)-F | 5.0% |
| 2O1-BEB (F)-C | 5.0% |
| 3O1-BEB (F)-C | 11.0% |
| 5O1-BEB (F)-C | 4.0% |
| 1V2-BEB (F, F)-C | 10.0% |
| 3-HH-EMe | 10.0% |
| 3-HB-O2 | 18.0% |
| 3-HHEB-F | 3.0% |
| 5-HHEB-F | 3.0% |
| 3-HBEB-F | 4.0% |
| 2O1-HBEB (F)-C | 2.0% |
| 3-HB (F) EB (F)-C | 2.0% |
| 3-HBEB (F, F)-C | 2.0% |
| 3-HHB-F | 4.0% |
| 3-HHB-O1 | 4.0% |
| 3-HHB-3 | 9.0% |
| 3-HEBEB-F | 2.0% |
| 3-HEBEB-1 | 2.0% |

$T_{NI} = 77.9$ (° C.)
$\eta = 39.3$ (mPa · s)
$\Delta n = 0.116$
$\Delta \kappa = 23.6$
$V_{th} = 0.99$ (V)

Example 11 (Use Example 8)

| | |
|---|---|
| 3-HH4B (F, F) B (F)-F | 3.0% |
| 5-BEB (F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 12.0% |
| 3-HHB-1 | 9.0% |
| 1V2-HBB-2 | 10.0% |
| 3-HHEBH-3 | 5.0% |

$T_{NI} = 91.4$ (° C.)
$\eta = 16.6$ (mPa · s)
$\Delta n = 0.117$
$\Delta \epsilon = 5.0$
$V_{th} = 2.30$ (V)

Example 12 (Use Example 9)

| | |
|---|---|
| 5-H4HB (F, F) B (F)-F | 4.0% |
| 3-HH4B (F, F) B (F)-F | 5.0% |
| 3-HH3OB (F, F) B (F)-F | 15.0% |
| 2O1-BEB (F)-C | 5.0% |
| 3O1-BEB (F)-C | 12.0% |
| 5O1-BEB (F)-C | 4.0% |
| 1V2-BEB (F, F)-C | 11.0% |
| 3-HB-O2 | 10.0% |
| 3-HH-4 | 3.0% |
| 3-HHB-F | 3.0% |
| 3-HHB-1 | 4.0% |
| 3-HHB-O1 | 4.0% |
| 3-HBEB-F | 4.0% |
| 5-HHEB-F | 7.0% |
| 3-H2BTB-4 | 4.0% |
| 3-HB (F) TB-2 | 5.0% |

$T_{NI} = 95.8$ (° C.)
$\eta = 55.0$ (mPa · s)
$\Delta n = 0.137$
$\Delta \epsilon = 27.4$
$V_{th} = 1.01$ (V)

Example 13 (Use Example 10)

| | |
|---|---|
| 5-H4HB (F, F) B (F)-F | 2.0% |
| 3-HH3OB (F, F) B (F)-F | 2.0% |
| 2-BEB-C | 12.0% |
| 3-BEB-C | 4.0% |
| 4-BEB-C | 6.0% |
| 3-HB-C | 28.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 3.0% |
| 3-HHB-O1 | 4.0% |

$T_{NI} = 63.0$ (° C.)
$\eta = 28.5$ (mPa · s)
$\Delta n = 0.113$
$\Delta \epsilon = 10.2$
$V_{th} = 1.34$ (V)

Example 14 (Use Example 11)

| | |
|---|---|
| 3-HH4B (F, F) B (F)-F | 5.0% |
| 3-HH3OB (F, F) B (F)-F | 10.0% |
| 3-HB-O2 | 5.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 3.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |

$T_{NI} = 69.8$ (° C.)

η = 29.0 (mPa · s)
Δn = 0.159
Δε = 7.3
$V_{th}$ = 1.76 (V)

Example 15 (Use Example 12)

| | |
|---|---|
| 3-H4BB (F, F) B (F)-F | 3.0% |
| 3-H3OB (F, F) B (F, F) B (F)-F | 3.0% |
| 3-H4B (F) B (F) B (F)-F | 3.0% |
| 1V2-BEB (F, F)-C | 5.0% |
| 3-HB-C | 26.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-HB (F) TB-2 | 6.0% |

Example 16 (Use Example 13)

| | |
|---|---|
| 5-H4B (F, F) B (F)-F | 2.0% |
| 3-H3OBB (F, F) B (F)-F | 3.0% |
| 3-H4B (F, F) B (F, F) B (F)-F | 2.0% |
| 3-H3OB (F) B (F) B (F)-F | 2.0% |
| V2-HB-C | 12.0% |
| 1V2-HB-C | 12.0% |
| 3-HB-C | 24.0% |
| 3-HB (F)-C | 5.0% |
| 2-BTB-1 | 2.0% |
| 3-HH-4 | 8.0% |
| 3-HH-VFF | 6.0% |
| 2-HHB-C | 3.0% |
| 3-HHB-C | 6.0% |
| 3-HB (F) TB-2 | 8.0% |
| 3-H2 BTB-2 | 5.0% |

Example 17 (Use Example 14)

| | |
|---|---|
| 5-H4HB (F, F) B (F)-F | 3.0% |
| 3-HH4B (F, F) B (F)-F | 5.0% |
| 2-HHB (F)-F | 17.0% |
| 3-HHB (F)-F | 5.0% |
| 5-HHB (F)-F | 16.0% |
| 7-HB (F)-F | 4.0% |
| 2-H2HB (F)-F | 10.0% |
| 3-H2HB (F)-F | 5.0% |
| 5-H2HB (F)-F | 10.0% |
| 2-HBB (F)-F | 6.0% |
| 3-HBB (F)-F | 6.0% |
| 5-HBB (F)-F | 13.0% |

$T_{NI}$ = 97.3 (° C.)
η = 29.1 (mPa · s)
Δn = 0.096
Δε = 5.1
$V_{th}$ = 2.20 (V)

Example 18 (Use Example 15)

| | |
|---|---|
| 3-HH4B (F, F) B (F)-F | 4.0% |
| 3-HH3OB (F, F) B (F)-F | 4.0% |
| 7-HB (F)-F | 7.0% |
| 5-H2B (F)-F | 5.0% |
| 3-HB-O2 | 10.0% |
| 3-HH-4 | 5.0% |
| 2-HHB (F)-F | 10.0% |
| 3-HHB (F)-F | 10.0% |
| 3-H2HB (F)-F | 5.0% |
| 2-HBB (F)-F | 3.0% |
| 3-HBB (F)-F | 3.0% |
| 5-HBB (F)-F | 6.0% |
| 2-H2BB (F)-F | 5.0% |
| 3-H2BB (F)-F | 6.0% |
| 3-HHB-1 | 8.0% |
| 3-HHB-O1 | 5.0% |
| 3-HHB-3 | 4.0% |

$T_{NI}$ = 88.7 (° C.)
η = 22.4 (mPa · s)
Δn = 0.095
Δε = 3.7
$V_{th}$ = 2.57 (V)

Example 19 (Use Example 16)

| | |
|---|---|
| 5-H4HB (F, F) B (F)-F | 3.0% |
| 3-HH3OB (F, F) B (F)-F | 5.0% |
| 7-HB (F, F)-F | 5.0% |
| 3-HB-O2 | 7.0% |
| 2-HHB (F)-F | 10.0% |
| 5-HHB (F)-F | 10.0% |
| 2-HBB (F)-F | 9.0% |
| 3-HBB (F)-F | 9.0% |
| 5-HBB (F)-F | 16.0% |
| 2-HBB-F | 4.0% |
| 3-HBB-F | 4.0% |
| 5-HBB-F | 3.0% |
| 3-HBB (F, F)-F | 5.0% |
| 5-HBB (F, F)-F | 10.0% |

$T_{NI}$ = 85.5 (° C.)
η = 30.3 (mPa · s)
Δn = 0.115
Δε = 6.0
$V_{th}$ = 1.98 (V)

Example 20 (Use Example 17)

| | |
|---|---|
| 5-H4HB (F, F) B (F)-F | 3.0% |
| 3-HH4B (F, F) B (F)-F | 3.0% |
| 3-HH3OB (F, F) B (F)-F | 3.0% |
| 7-HB (F, F)-F | 7.0% |
| 3-H2HB (F, F)-F | 12.0% |
| 4-H2HB (F, F)-F | 10.0% |
| 5-H2HB (F, F)-F | 10.0% |
| 3-HHB (F, F)-F | 10.0% |
| 4-HHB (F, F)-F | 5.0% |
| 3-HH2B (F, F)-F | 3.0% |
| 5-HH2B (F, F)-F | 10.0% |
| 3-HBB (F, F)-F | 12.0% |
| 5-HBB (F, F)-F | 12.0% |

$T_{NI}$ = 92.0 (° C.)
η = 20.4 (mPa · s)
Δn = 0.127
Δε = 5.1
$V_{th}$ = 2.28 (V)

Example 21 (Use Example 18)

| | |
|---|---|
| 5-H4HB (F, F) B (F)-F | 3.0% |
| 7-HB (F, F)-F | 7.0% |
| 3-H2HB (F, F)-F | 12.0% |
| 4-H2HB (F, F)-F | 10.0% |
| 3-HHB (F, F)-F | 10.0% |
| 4-HHB (F, F)-F | 5.0% |
| 3-HBB (F, F)-F | 10.0% |
| 3-HHEB (F, F)-F | 5.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 5.0% |
| 5-HBEB (F, F)-F | 3.0% |
| 3-HDB (F, F)-F | 15.0% |
| 3-HHBB (F, F)-F | 6.0% |

$T_{NI}$ = 74.3 (° C.)
η = 34.8 (mPa · s)
Δn = 0.084
Δε = 13.0
$V_{th}$ = 1.39 (V)

Example 22 (Use Example 19)

| | |
|---|---|
| 3-HH3OB (F, F) B (F)-F | 4.0% |
| 3-HB-CL | 10.0% |
| 5-HB-CL | 4.0% |
| 7-HB-CL | 4.0% |
| 3-HB-O2 | 2.0% |
| 1O1-HH-5 | 5.0% |
| 2-HBB (F)-F | 8.0% |
| 3-HBB (F)-F | 8.0% |
| 5-HBB (F)-F | 8.0% |
| 4-HHB-CL | 8.0% |
| 5-HHB-CL | 8.0% |
| 3-H2HB (F)-CL | 4.0% |
| 3-HBB (F, F)-F | 10.0% |
| 5-H2BB (F, F)-F | 9.0% |

-continued

| | |
|---|---|
| 3-HB (F) VB-2 | 4.0% |
| 3-HB (F) VB-3 | 4.0% |
| $T_{NI} = 92.0$ (° C.) | |
| $\eta = 20.4$ (mPa·s) | |
| $\Delta n = 0.127$ | |
| $\Delta\epsilon = 5.1$ | |
| $V_{th} = 2.28$ (V) | |

Example 23 (Use Example 20)

| | |
|---|---|
| 3-HH3OB (F, F) B (F)-F | 5.0% |
| 7-HB (F, F)-F | 4.0% |
| 3-HHB (F, F)-F | 9.0% |
| 3-H2HB (F, F)-F | 8.0% |
| 4-H2HB (F, F)-F | 8.0% |
| 5-H2HB (F, F)-F | 8.0% |
| 3-HBB (F, F)-F | 21.0% |
| 5-HBB (F, F)-F | 11.0% |
| 3-H2BB (F, F)-F | 10.0% |
| 5-HHBB (F, F)-F | 3.0% |
| 3-HH2BB (F, F)-F | 3.0% |
| 5-HHEBB-F | 2.0% |
| 1O1-HBBH-4 | 4.0% |
| 1O1-HBBH-5 | 4.0% |
| $T_{NI} = 97.6$ (° C.) | |
| $\eta = 36.3$ (mPa·s) | |
| $\Delta n = 0.113$ | |
| $\Delta\epsilon = 8.9$ | |
| $V_{th} = 1.77$ (V) | |

Example 24 (Use Example 21)

| | |
|---|---|
| 5-H4HB (F, F) B (F)-F | 2.0% |
| 3-HH4B (F, F) B (F)-F | 2.0% |
| 5-HB-F | 12.0% |
| 6-HB-F | 9.0% |
| 7-HB-F | 9.0% |
| 2-HHB-OCF3 | 7.0% |
| 3-HHB-OCF3 | 5.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB (F, F)-OCF3 | 5.0% |
| 3-HBB (F)-F | 10.0% |
| 5-HBB (F)-F | 10.0% |
| 3-HH2B (F)-F | 3.0% |
| 3-HB (F) BH-3 | 3.0% |
| 5-HBBH-3 | 3.0% |
| $T_{NI} = 85.5$ (° C.) | |
| $\eta = 16.3$ (mPa·s) | |
| $\Delta n = 0.092$ | |
| $\Delta\epsilon = 4.6$ | |
| $V_{th} = 2.38$ (V) | |

Example 25 (Use Example 22)

| | |
|---|---|
| 3-HH3OB (F, F) B (F)-F | 3.0% |
| 7-HB (F)-F | 2.0% |
| 5-H4HB (F, F)-F | 7.0% |
| 5-H4HB-OCF3 | 15.0% |
| 3-H4HB (F, F)-CF3 | 8.0% |
| 5-H4HB (F, F)-CF3 | 5.0% |
| 3-HB-CL | 6.0% |
| 5-HB-CL | 4.0% |
| 2-H2BB (F)-F | 5.0% |
| 3-H2BB (F)-F | 10.0% |
| 5-HVHB (F, F)-F | 5.0% |
| 3-HHB-OCF3 | 5.0% |
| 3-H2HB-OCF3 | 5.0% |
| V-HHB (F)-F | 5.0% |
| 3-HChB (F)-F | 5.0% |
| 5-HHEB-OCF3 | 2.0% |
| 3-HBEB (F, F)-F | 5.0% |
| 5-HH-V2F | 3.0% |
| $T_{NI} = 71.3$ (° C.) | |
| $\eta = 24.9$ (mPa·s) | |
| $\Delta n = 0.088$ | |
| $\Delta\epsilon = 8.0$ | |
| $V_{th} = 1.77$ (V) | |

Example 26 (Use Example 23)

| | |
|---|---|
| 5-H4HB (F, F) B (F)-F | 2.0% |
| 3-HH4B (F, F) B (F, F)-F | 3.0% |
| 3-HH3OB (F, F) B (F)-F | 10.0% |
| 7-HB (F, F)-F | 10.0% |
| 3-HB-O2 | 5.0% |
| 2-HHB (F)-F | 2.0% |
| 3-HHB (F)-F | 2.0% |
| 5-HHB (F)-F | 2.0% |
| 2-HBB (F)-F | 6.0% |
| 3-HBB (F)-F | 6.0% |
| 2-H2BB (F)-F | 9.0% |
| 3-H2BB (F)-F | 9.0% |
| 3-HBB (F, F)-F | 5.0% |
| 5-HBB (F, F)-F | 19.0% |
| 1O1-HBBH-4 | 5.0% |
| 1O1-HBBH-5 | 5.0% |
| $T_{NI} = 94.4$ (° C.) | |
| $\eta = 36.0$ (mPa·s) | |
| $\Delta n = 0.121$ | |
| $\Delta\epsilon = 6.9$ | |
| $V_{th} = 1.98$ (V) | |

Example 27 (Use Example 24)

| | |
|---|---|
| 5-H4B (F, F) BB (F)-F | 3.0% |
| 3-H3OBB (F, F) B (F)-F | 5.0% |
| 2-HHB (F)-F | 17.0% |
| 3-HHB (F)-F | 5.0% |
| 5-HHB (F)-F | 16.0% |
| 7-HB (F)-F | 4.0% |
| 2-H2HB (F)-F | 10.0% |
| 3-H2HB (F)-F | 5.0% |
| 5-H2HB (F)-F | 10.0% |
| 2-HBB (F)-F | 6.0% |
| 3-HBB (F)-F | 6.0% |
| 5-HBB (F)-F | 13.0% |

Example 28 (Use Example 25)

| | |
|---|---|
| 5-H4B (F, F) BB (F)-F | 3.0% |
| 3-H4BB (F, F) B (F)-F | 3.0% |
| 3-H3OBB (F, F) B (F)-F | 3.0% |
| 7-HB (F, F)-F | 7.0% |
| 3-H2HB (F, F)-F | 12.0% |
| 4-H2HB (F, F)-F | 10.0% |
| 5-H2HB (F, F)-F | 10.0% |
| 3-HHB (F, F)-F | 10.0% |
| 4-HHB (F, F)-F | 5.0% |
| 3-HH2B (F, F)-F | 7.0% |
| 5-HH2B (F, F)-F | 6.0% |
| 3-HBB (F, F)-F | 12.0% |
| 5-HBB (F, F)-F | 12.0% |

Example 29 (Use Example 26)

| | |
|---|---|
| 3-H4B (F, F) B (F, F) B (F)-F | 2.0% |
| 3-H3OB (F, F) B (F, F) B (F)-F | 2.0% |
| 3-H4B (F) B (F) B (F)-F | 2.0% |
| 3-H3OB (F) B (F) B (F)-F | 2.0% |
| 7-HB (F, F)-F | 5.0% |
| 3-HB-O2 | 7.0% |
| 2-HHB (F)-F | 10.0% |
| 3-HHB (F)-F | 10.0% |
| 2-HBB (F)-F | 9.0% |
| 3-HBB (F)-F | 9.0% |
| 5-HBB (F)-F | 16.0% |
| 2-HBB-F | 4.0% |
| 3-HBB-F | 4.0% |
| 5-HBB-F | 3.0% |
| 3-HBB (F, F)-F | 5.0% |
| 5-HBB (F, F)-F | 10.0% |

What is claimed is:

1. A difluorophenyl derivative compound represented by the general formula (1):

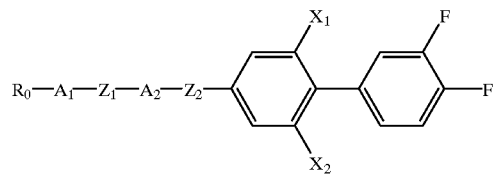
(1)

wherein $R_0$ is an alkyl group or an alkenyl group having 1 to 15 carbon atoms, and an optional methylene group (—CH$_2$—) in the alkyl group or the alkenyl group may be substituted by an oxygen atom (—O—), but 2 or more methylene groups are not consecutively substituted by the oxygen atoms; $A_1$ and $A_2$ are each independently a trans-1, 4-cyclohexylene group, or one group selected from the group consisting of a 1,4-phenylene group, a pyrimidine-2, 5-diyl group, a pyridine-2,5-diyl group, a 1,3-dioxane-2,5-diyl group, a tetrahydropyran-2,5-diyl group, a 1,3-dithian-2,5-diyl group and a tetrahydrothiopyran-2,5-diyl in which one or more hydrogen atoms on a six-membered ring may be substituted by halogen atoms; $Z_1$ and $Z_2$ are each independently —(CH$_2$)$_4$—, —(CH$_2$)$_3$O—, —O(CH$_2$)$_3$— or a single bond in which at least one of $Z_1$ and $Z_2$ is —(CH$_2$)$_4$—, —(CH$_2$)$_3$O—, or —O(CH$_2$)$_3$—; $X_1$ and $X_2$ are each independently H, F, Cl or Br.

2. The difluorophenyl derivative compound according to claim 1 wherein $Z_1$ is —(CH$_2$)$_4$— or —(CH$_2$)$_3$O—; $Z_2$ is a single bond; $A_1$ is a trans-1,4-cyclohexylene group; $A_2$ is a trans-1,4-cyclohexylene group or a 1,4-phenylene group; and $X_1$ and $X_2$ are each a hydrogen atom.

3. The difluorophenyl derivative compound according to claim 1 wherein $Z_1$ is —(CH$_2$)$_4$— or —(CH$_2$)$_3$O—; $Z_2$ is a single bond; $A_1$ is a trans-1,4-cyclohexylene group; $A_2$ is a trans-1,4-cyclohexylene group or a 1,4-phenylene group; and $X_1$ and/or $X_2$ is a fluorine atom.

4. The difluorophenyl derivative compound according to claim 1 wherein $Z_1$ is a single bond; $Z_2$ is —(CH$_2$)$_4$— or —(CH$_2$)$_3$O—; $A_1$ is a trans-1,4-cyclohexylene group; $A_2$ is a trans-1,4-cyclohexylene group or a 1,4-phenylene group; and $X_1$ and $X_2$ are each a hydrogen atom.

5. The difluorophenyl derivative compound according to claim 1 wherein $Z_1$ is a single bond; $Z_2$ is —(CH$_2$)$_4$— or —(CH$_2$)$_3$O—; $A_1$ is a trans-1,4-cyclohexylene group; $A_2$ is a trans-1,4-cyclohexylene group or a 1,4-phenylene group; and $X_1$ and/or $X_2$ is a fluorine atom.

6. A liquid crystal composition which comprises 2 or more components containing at least one difluorophenyl derivative compound described in claim 1.

7. A liquid crystal composition which comprises at least one difluorophenyl derivative compound described in claim 1 as a first component, and at least one compound selected from the group consisting of the general formulae (2), (3) and (4) as a second component:

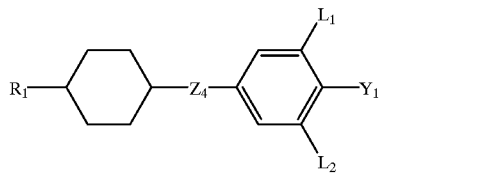
(2)

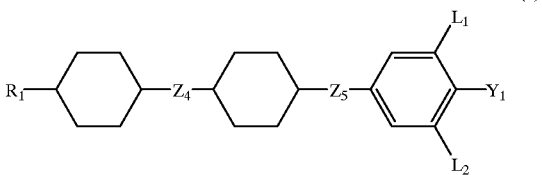
(3)

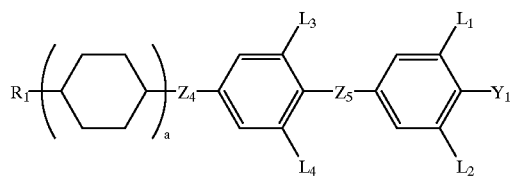
(4)

wherein $R_1$ is an alkyl group having 1 to 10 carbon atoms; $Y_1$ is F, Cl, OCF$_3$, OCF$_2$H, CF$_3$, CF$_2$H or CFH$_2$; and $L_1$, $L_2$, $L_3$ and $L_4$ are each independently H or F; $Z_4$ and $Z_5$ are each independently —(CH$_2$)$_2$—, —CH═CH— or a single bond; and a is 1 or 2.

8. A liquid crystal composition which comprises at least one difluorophenyl derivative compound described in claim 1 as a first component, and at least one compound selected from the group consisting of the general formulae (5), (6), (7), (8) and (9) as a second component:

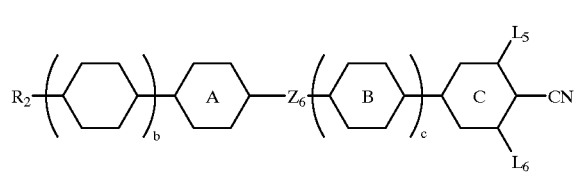
(5)

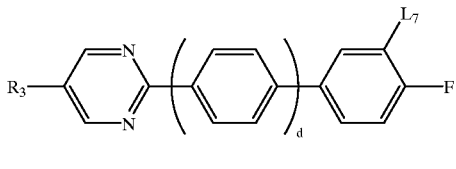
(6)

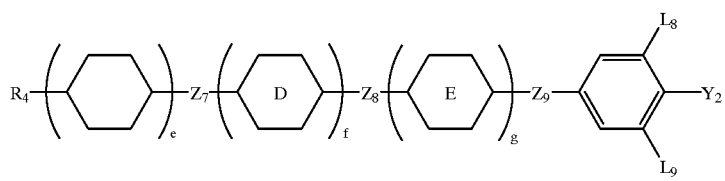
(7)

-continued

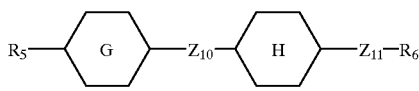

(8)

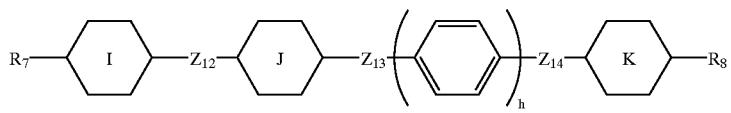

(9)

in the general formula (5), $R_2$ is F, an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring A is a trans-1,4-cyclohexylene group, a 1,4-phenylene group, a pyrimidine-2,5-diyl group or a 1,3-dioxane-2,5-diyl group; a ring B is a trans-1,4-cyclohexylene group, a 1,4-phenylene group or a pyrimidine-2,5-diyl group; a ring C is a trans-1,4-cyclohexylene group or a 1,4-phenylene group; $Z_6$ is —$(CH_2)_2$—, —COO— or a single bond; $L_5$ and $L_6$ are each independently H or F; and b and c are each independently 0 or 1, in the general formula (6), $R_3$ is an alkyl group having 1 to 10 carbon atoms; $L_7$ is H or F; and d is 0 or 1, in the general formula (7), $R_4$ is an alkyl group having 1 to 10 carbon atoms; a ring D and a ring E are each independently a trans-1,4-cyclohexylene group or a 1,4-phenylene group; $Z_7$ and $Z_8$ are each independently —COO— or a single bond; $Z_9$ is —COO— or —C≡C—; $L_8$ and $L_9$ are each independently H or F; $Y_2$ is F, $OCF_3$, $OCF_2H$, $CF_3$, $CF_2H$ or $CFH_2$; and e, f and g are each independently 0 or 1, in the general formula (8), $R_5$ and $R_6$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring G is a trans-1,4-cyclohexylene group, a 1,4-phenylene group or a pyrimidine-2,5-diyl group; a ring H is a trans-1,4-cyclohexylene group or a 1,4-phenylene group; $Z_{10}$ is —C≡C—, —COO—, —$(CH_2)_2$—, —CH=CH—C≡C— or a single bond; and $Z_{11}$ is —COO— or a single bond, and in the general formula (9), $R_7$ and $R_8$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not continuously substituted by the oxygen atoms; a ring I is a trans-1,4-cyclohexylene group, a 1,4-phenylene group or a pyrimidine-2,5-diyl group; a ring J is a trans-1,4-cyclohexylene group or a 1,4-phenylene group in which one or more hydrogen atoms on the ring may be substituted by F, or a pyrimidine-2,5-diyl group; a ring K is a trans-1,4-cyclohexylene group or a 1,4-phenylene group; $Z_{12}$ and $Z_{14}$ are each independently —COO—, —$(CH_2)_2$— or a single bond; $Z_{13}$ is —CH=CH—, —C≡C—, —COO— or a single bond; and h is 0 or 1.

9. A liquid crystal display device comprising the liquid crystal composition described in claim 6.

10. A liquid crystal composition which comprises:
at least one liquid crystal compound described in claim 1 as a first component;
at least one compound selected from the group consisting of the general formulae (2), (3) and (4) as a second component:

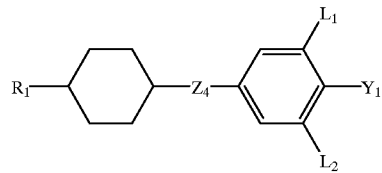

(2)

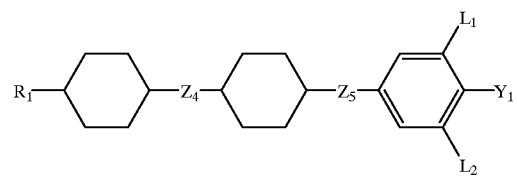

(3)

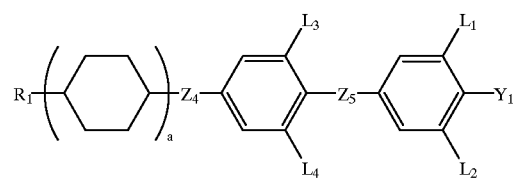

(4)

wherein $R_1$ is an alkyl group having 1 to 10 carbon atoms; $Y_1$ is F, Cl, $OCF_3$, $OCF_2H$, $CF_3$, $CF_2H$, or $CFH_2$; and $L_1$, $L_2$, $L_3$ and $L_4$ are each independently H or F; $Z_4$ and $Z_5$ are each independently —$(CH_2)_2$—, —CH=CH— or single bond; and a is 1 or 2; and at least one compound selected from the groups consisting of the general formulae (5), (6), (7), (8) and (9) as a third component:

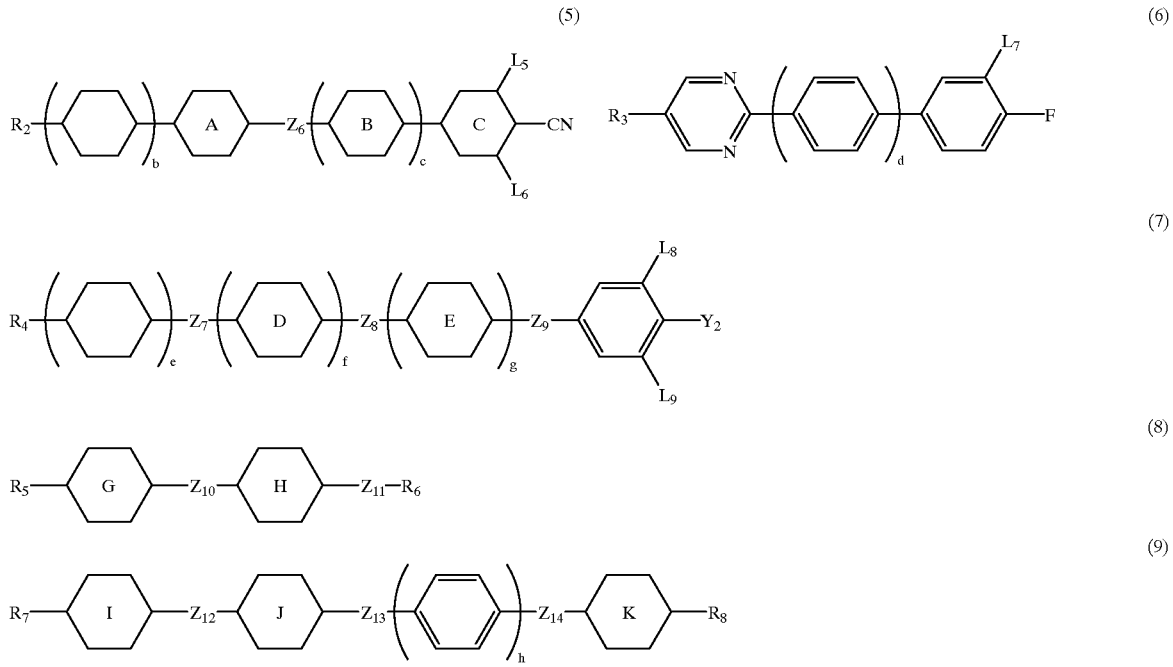

in the general formula (5), $R_2$ is F, an alkyl group having 1 to 10 carbon atoms or an alkenyl group having 2 to 10 carbon atoms, and an optional methylene group (—$CH_2$) in the alkyl group or the alkenyl group may be substituted by an oxygen atom (—O—), but 2 or more methylene groups are not consecutively substituted by the oxygen atoms; a ring A is a trans-1,4-cyclohexylene group, a 1,4-phenylene group, a pyrimidine-2,5-diyl group or a 1,3-dioxane-2,5-diyl group; a ring B is a trans-1,4-cyclohexylene group, a 1,4-phenylene group or a pyrimidine-2,5-diyl group; a ring C is a trans-1,4-cyclohexylene group or a 1,4-phenylene group; $Z_6$ is —$(CH_2)_2$—, —COO— or a single bond; $L_5$ and $L_6$ are each independently H or F; and b and c are each independently 0 or 1;

in the general formula (6), $R_3$ is an alkyl group having 1 to 10 carbon atoms; $L_7$ is H or F; and d is 0 or 1;

in the general formula (7), $R_4$ is an alkyl group having 1 to 10 carbon atoms; a ring D and a ring E are each independently a trans-1,4-cyclohexylene group or a 1,4-phenylene group; $Z_7$ and $Z_8$ are each independently —COO— or a single bond; $Z_9$ is —COO— or —C≡C—; $L_8$ and $L_9$ are each independently H or F; $Y_2$ is F, $OCF_3$, $OCF_2H$, $CF_3$, $CF_2H$ or $CFH_2$; and e, f, and g are each independently 0 or 1;

in the general formula (8); $R_5$ and $R_6$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not consecutively substituted by the oxygen atoms; a ring G is a trans-1,4-cyclohexylene group, a 1,4-phenylene group or a pyrimidine-2,5-diyl group; a ring H is a trans-1,4-cyclohexylene group or a 1,4-phenylene group; $Z_{10}$ is —C≡C—, —COO—, —$(CH_2)_2$—, —CH=CH—C≡C— or a single bond; and $Z_{11}$ is —COO— or a single bond; and in the general formula (9), $R_7$ and $R_8$ are each independently an alkyl group having 1 to 10 carbon atoms or an alkenyl group having 2 to 10 carbon atoms, and an optional methylene group (—$CH_2$—) in the alkyl group or the alkenyl group may be substituted by an oxygen atom (—O—), but 2 or more methylene groups are not consecutively substituted by the oxygen atoms; a ring I is a trans-1,4-cyclohexylene group, a 1,4-phenylene group or a pyrimidine-2,5-diyl group; a ring J is a trans-1,4-cyclohexylene group or a 1,4-phenylene group in which one or more hydrogen atoms on the ring may be substituted by F, or a pyrimidine-2,5-diyl group; a ring K is a trans-1,4-cyclohexylene group or a 1,4-phenylene group; $Z_{12}$ and $Z_{14}$ are each independently —COO—, —$(CH_2)_2$— or a single bond; $Z_{13}$ is —CH=CH—, —C≡C—, —COO— or a single bond; and h is 0 or 1.

* * * * *